United States Patent
Hao et al.

(10) Patent No.: US 11,466,029 B2
(45) Date of Patent: Oct. 11, 2022

(54) COMPOUNDS USEFUL TO TREAT INFLUENZA VIRUS INFECTIONS

(71) Applicant: Nanjing Zhengxiang Pharmaceuticals Co., Ltd., Jiangsu (CN)

(72) Inventors: Xiaolin Hao, Foster City, CA (US); Jinfu Yang, Foster City, CA (US)

(73) Assignee: NANJING ZHENGXIANG PHARMACEUTICALS CO., LTD., Nanjing (CN)

( * ) Notice: Subject to any disclaimer, the term of this patent is extended or adjusted under 35 U.S.C. 154(b) by 0 days.

(21) Appl. No.: 17/569,367

(22) Filed: Jan. 5, 2022

(65) Prior Publication Data

US 2022/0127282 A1   Apr. 28, 2022

Related U.S. Application Data

(63) Continuation of application No. 17/297,407, filed as application No. PCT/US2020/041578 on Jul. 10, 2020.

(60) Provisional application No. 62/944,309, filed on Dec. 5, 2019, provisional application No. 62/872,998, filed on Jul. 11, 2019.

(51) Int. Cl.
  *C07D 498/14*   (2006.01)
  *A61P 31/16*    (2006.01)
  *C07F 9/6561*   (2006.01)

(52) U.S. Cl.
  CPC .......... *C07D 498/14* (2013.01); *A61P 31/16* (2018.01); *C07F 9/6561* (2013.01)

(58) Field of Classification Search
  CPC ....... C07D 498/14; A61P 31/16; C07F 9/6561
  USPC ...................................................... 514/120
  See application file for complete search history.

(56) References Cited

U.S. PATENT DOCUMENTS

2018/0118760 A1   5/2018   Kawai et al.
2022/0033416 A1   2/2022   Hao et al.

OTHER PUBLICATIONS

Gu, R.-X. et al., (Oct. 2013). "Structural and Energetic Analysis of Drug Inhibition of the Influenza A M2 Proton Channel," Trends Pharmacol Sci. 34:571-580.
International Search Report and Written Opinion for International Patent Application No. PCT/US2020/41578, dated Dec. 3, 2020, 11 pages.
Luliano, A.D. et al., (Mar. 31, 2018). "Estimates of Global Seasonal Influenza-Associated Respiratory Mortality: A Modelling Study," Lancet 391 (10127):1285-1300, 31 pages.
Maroney, M.J. et al., (Nov. 1, 2018). "Selenium Versus Sulfur: Reversibility of Chemical Reactions and Resistance to Permanent Oxidation in Proteins and Nucleic Acids," Free Radie Biol Med. 127:228-237, 30 pages.
Nozawa, R. et al. (Aug. 1989). "Susceptibility of Methicillin-Resistant *Staphylococcus aureus* to the Selenium-Containing Compound 2-Phenyl-1,2-Benzoisoselenazol-3(2H)-One (PZ51)", Antimicrobial Agents and Chemotherapy 33(8):1388-1390.
Omoto, S. et al., (2018, e-pub. Jun. 25, 2018). "Characterization of Influenza Virus Variants Induced by Treatment With the Endonuclease Inhibitor Baloxavir Marboxil," Scientific Reports, 8:9633, 15 pages.
Roy, G. et al., (2008). "Selenium Analogues of Antithyroid Drugs-Recent Developments," Chemistry and Biodiversity, 5:414-439.
Stevaert, A. et al., (2016). "The Influenza Virus Polymerase Complex: An Update on its Structure, Functions, and Significance for Antiviral Drug Design," Medicinal Research Reviews, 36(6):1127-1173.
World Health Organization, (2019). "WHO: Global Influenza Strategy 2019-2030," Available online at https://apps.who.int/iris/handle/10665/311184, 34 pages.
International Preliminary Report on Patentability, dated Jan. 11, 2022, for PCT Application No. PCT/US2020/41578, filed Jul. 10, 2020, 7 pages.

*Primary Examiner* — Kahsay Habte
(74) *Attorney, Agent, or Firm* — Morrison & Foerster LLP

(57) ABSTRACT

The invention provides compounds that may inhibit influenza virus replication, and are accordingly useful for treatment of viral infections caused by influenza virus. The invention further provides pharmaceutical compositions containing these compounds and methods of using these compounds to treat or prevent viral infections caused by influenza virus.

18 Claims, 2 Drawing Sheets

US 11,466,029 B2

COMPOUNDS USEFUL TO TREAT INFLUENZA VIRUS INFECTIONS

CROSS REFERENCE TO RELATED APPLICATIONS

This application is a continuation of U.S. patent application Ser. No. 17/297,407, filed May 26, 2021, which is a national stage application under 35 U.S.C. § 371 of International Application No. PCT/US2020/041578, filed internationally on Jul. 10, 2020, which claims prior benefit of U.S. Provisional Patent Application No. 62/872,998, filed Jul. 11, 2019, and U.S. Provisional Patent Application Ser. No. 62/944,309, filed Dec. 5, 2019, the disclosures of each of which are hereby incorporated by reference in their entirety.

FIELD OF THE INVENTION

This disclosure relates generally to compounds and compositions that may be useful for treatment of viral infections.

BACKGROUND

Influenza occurs in annual outbreaks each fall and winter worldwide. Influenza typically causes a self-limited respiratory illness with fever that lasts from 3 to 7 days. In spite of the availability of influenza vaccines, across the globe, there are an estimated 1 billion cases of influenza, 3-5 million are severe cases and 290000-650000 lead to influenza-related respiratory deaths each year (WHO: Global Influenza Strategy 2019-2030 and Iuliano AD et al. Lancet. 2018, 391, 1285-300).

Influenza viruses belong to the family Orthomyxoviridae, which are enveloped viruses containing a single-stranded, negative-sense RNA genome. Two classes of anti-Influenza viruses therapies, M2 ion-channel inhibitors and neuraminidase inhibitors, are commonly available in the past decades. However, resistance to M2 ion-channel inhibitors has been widely observed, and the emergence of antiviral resistance to neuraminidase inhibitors remains a threat. Matrix Protein 2 (M2) Inhibitors, Rimantadine and Amantadine, inhibit influenza A virus replication by occluding the M2 proton channel, but lack activity against influenza B virus (Gu R, Liu LA, Wei D, Trends Pharmacol Sci 2013, 34, 571).

Additional effective antiviral agents are needed for the treatment and prevention of influenza virus infections. Influenza viral RNA—dependent RNA polymerase (RdRp) with endonuclease activity cleaves a section of the capped 5'-end of cellular mRNA and use them to prime transcription of viral mRNA, the process known as "cap-snatching". A ribonucleoprotein complex composed of PA, PB1 and PB2 subunits, is responsible and essential for the "cap-snatching" process. The influenza virus polymerase complex has received considerable attention as a target to small molecule inhibitors for the treatment of influenza virus infection (Stevaert, A. & Naesens, L, Medicinal Research Reviews 2016, 36, 1127-1173). In 2018, baloxavir marboxil (Xofluza), a cap-dependent endonuclease (CEN) inhibitor, was approved in the US and Japan for treatment of influenza A and influenza B. Baloxavir marboxil is a prodrug that is converted through hydrolysis to its active form, baloxavir. Baloxavir inhibits influenza virus polymerase acidic (PA) protein endonuclease resulting in inhibition of viral RNA synthesis. However, in 2.2% of recipients in the phase 2 trial and in about 10% of recipients in the phase 3 trial, the influenza strain became resistant, which was due to I38T/M/F mutants (Shinya 0 et al., Scientific Reports 2018, 8, 9633). Furthermore, baloxavir marboxil and its active component baloxavir have poor oral availability.

Therefore, there is an urgent need to develop new therapeutics that have improved pharmaceutical and/or biological properties.

BRIEF DESCRIPTION OF THE FIGURES

FIG. 1A shows the body weight change and FIG. 1B shows the percent survival, when Compound B-1, Compound C-1, Oseltamivir Phosphate or vehicle was administered.

SUMMARY OF THE INVENTION

Figure 1A:
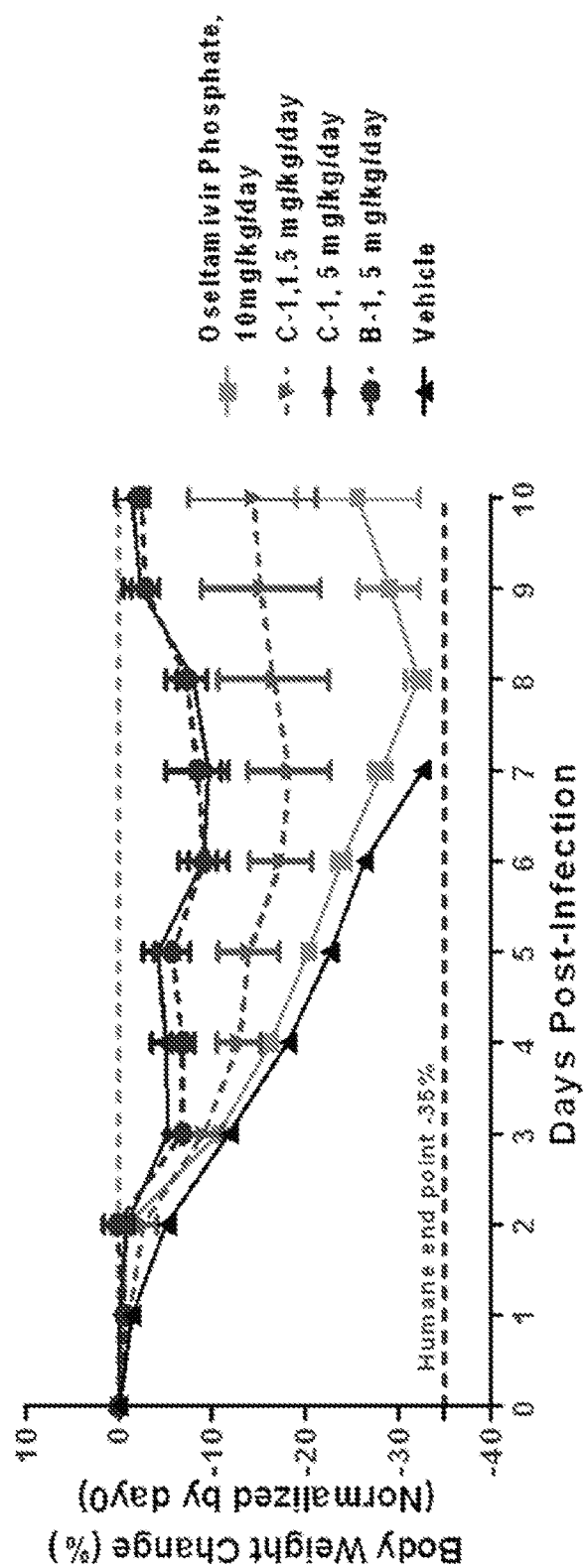
FIG. 1A and FIG. 1B illustrate antivirus efficacy in influenza virus PR/8/34 mouse model.

In one aspect, provided is a compound of Formula (I):

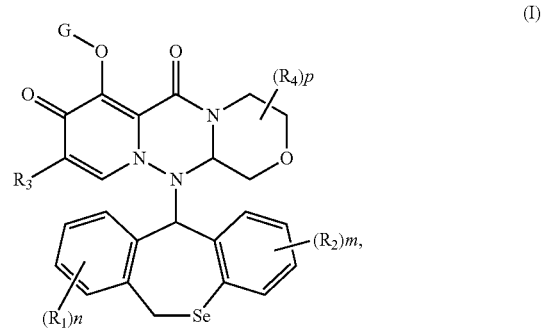

or a pharmaceutically acceptable salt, stereoisomer or solvate thereof, wherein $R_1$, $R_2$, $R_3$, $R_4$, m, n, p, and G are as detailed herein.

In one aspect, provided is a compound of Formula (II):

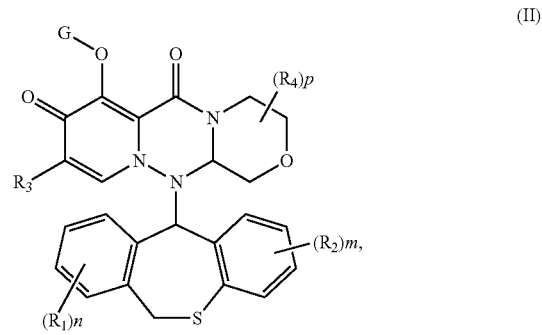

or a pharmaceutically acceptable salt, stereoisomer or solvate thereof, wherein $R_1$, $R_2$, $R_3$, $R_4$, m, n, p, and G are as detailed herein.

In some embodiments, the compound of Formula (I) or (II), or a pharmaceutically acceptable salt, stereoisomer or solvate thereof, is of Formula (I-1), (I-2), (I-3), (II-1), (II-2), or (II-3), as detailed herein.

In another aspect, provided is a method of treating or preventing influenza virus infections.

In some embodiments, provided is a method of treating influenza, comprising administering to a subject in need thereof a therapeutically effective amount of a compound of Formula (I) or (II), or pharmaceutically acceptable salt, stereoisomer or solvate thereof.

Also provided are pharmaceutical compositions comprising: (A) a compound detailed herein, such as a compound of Formula (I) or (II), or a pharmaceutically acceptable salt, stereoisomer or solvate thereof; and (B) a pharmaceutically acceptable carrier or excipient. Kits comprising a compound detailed herein or a pharmaceutically acceptable salt, stereoisomer or solvate thereof and optionally instructions for use are also provided.

Compounds as detailed herein or a pharmaceutically acceptable salt, stereoisomer or solvate thereof are provided for use as a medicament. Compounds as detailed herein or a pharmaceutically acceptable salt, stereoisomer or solvate thereof are also provided for the manufacture of a medicament for the treatment or prevention of influenza virus infections.

Compounds as detailed herein or a pharmaceutically acceptable salt, stereoisomer or solvate thereof show superior pharmacokinetic properties and biological activities. For example, there is no food effect to pharmacokinetic parameters in cynomolgus monkeys: oral bioavailabilities of fasted and fed monkey are both more than 50%. Therefore, compounds as detailed herein or a pharmaceutically acceptable salt, stereoisomer or solvate thereof show great advantages.

DETAILED DESCRIPTION

Definitions

For use herein, unless clearly indicated otherwise, use of the terms "a", "an" and the like refers to one or more.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in connection with a value, contemplate a variation within ±15%, within ±10%, within ±5%, within ±4%, within ±3%, within ±2%, within ±1%, or within ±0.5% of the specified value. Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{10}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_{10}$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Heterocycle" or "heterocyclic" or "heterocycloalkyl" or "heterocyclyl" refers to a saturated or partially saturated, but not aromatic, group having from 1 to 10 ring carbon atoms, preferably from 1 to 8 carbon atoms, and more preferably from 1 to 6 carbon atoms, and from 1 to 4 ring heteroatoms, preferably from 1 to 3 heteroatoms, and more preferably from 1 to 2 heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—CF3).

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases which can be used to prepared salts include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Stereoisomer" or "stereoisomers" refer to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of an individual.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount is an amount sufficient to delay development. In some embodiments, an effective amount is an amount sufficient to prevent or delay recurrence. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "subject" is a mammal, including humans. A subject includes, but is not limited to, human, bovine, horse, feline, canine, rodent, or primate. In some embodiments, the subject is human.

Unless otherwise stated, "substantially pure" intends a composition that contains no more than 10% impurity, such as a composition comprising less than about 9%, 7%, 5%, 3%, 1%, 0.5% impurity.

It is understood that aspects and variations described herein also include "consisting" and/or "consisting essentially of" aspects and variations.

All references throughout, such as publications, patents, patent applications and published patent applications, are incorporated herein by reference in their entireties.

Compounds

In one aspect, the invention provides a compound of Formula (I):

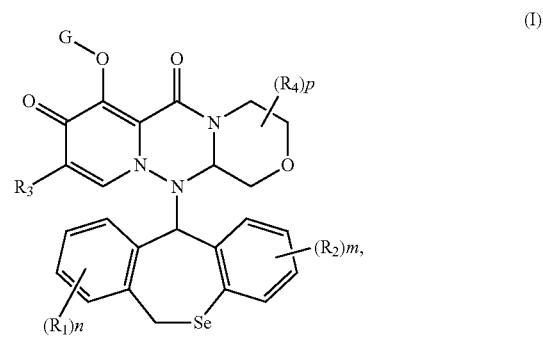

or a pharmaceutically acceptable salt, stereoisomer or solvate thereof, wherein:

each $R_1$ is independently selected from the group consisting of H and halo;

each $R_2$ is independently selected from the group consisting of H and halo;

$R_3$ is selected from the group consisting of H, halo, Me, CN, and $P(O)Me_2$;

each $R_4$ is independently selected from the group consisting of $C_1$-$C_6$ alkyl and $C_3$-$C_6$ cycloalkyl, wherein any two of $R_4$ are optionally taken, together with the atoms to which they are attached, to form a $C_3$-$C_6$ cycloalkyl;

n and m are each independently 0, 1, 2, 3, or 4;

p is 0, 1, 2, or 3; and

G is H or is selected from the group consisting of C(O)R, C(O)OR, C(O)NR'R, C(R')$_2$—O—C(O)R, C(R')$_2$—O—C(O)OR, and C(R')$_2$—O—C(O)NR'R, wherein each R is selected from the group consisting of $C_1$-$C_{10}$ alkyl, phenyl, pyridyl, $C_3$-$C_6$ cycloalkyl, and a 4-6 membered heterocyclic ring containing one or two heteroatoms selected from the group consisting of N, O and S as ring members, wherein the $C_1$-$C_{10}$ alkyl, phenyl, pyridyl, $C_3$-$C_6$ cycloalkyl, and 4-6 membered heterocyclic ring of R are independently optionally substituted with one or two substituents selected from the group consisting of H, halo, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy; and each R' is independently selected from the group consisting of H and $C_1$-$C_3$ alkyl.

In some embodiments, provided is a compound of Formula (I-1):

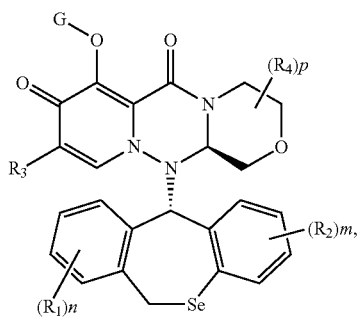

(I-1)

or a pharmaceutically acceptable salt, stereoisomer or solvate thereof, wherein $R_1$, $R_2$, $R_3$, $R_4$, m, n, p, and G are as detailed herein for Formula (I).

In some embodiments, provided is a compound of Formula (I-2):

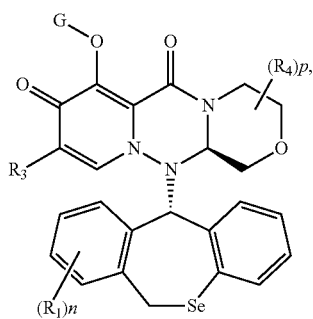

(I-2)

or a pharmaceutically acceptable salt, stereoisomer or solvate thereof, wherein $R_1$, n, and G are as detailed herein for Formula (I).

In some embodiments, provides is a compound selected from the group consisting of:

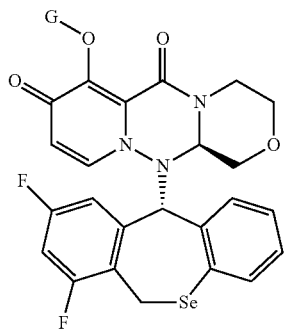

-continued

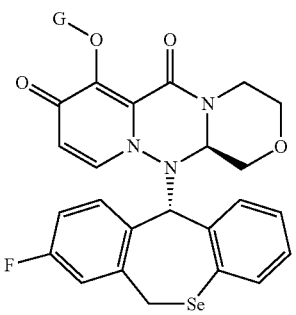

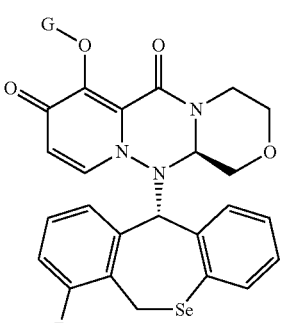

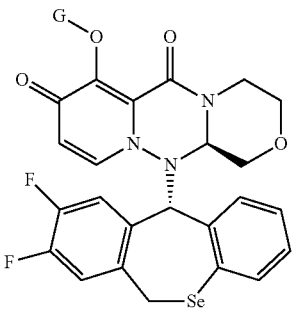

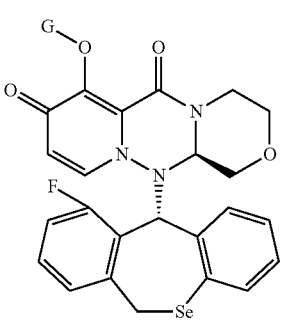

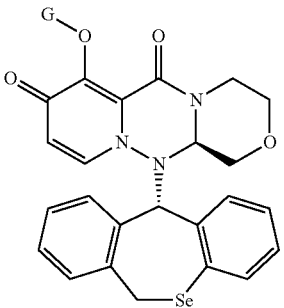

-continued

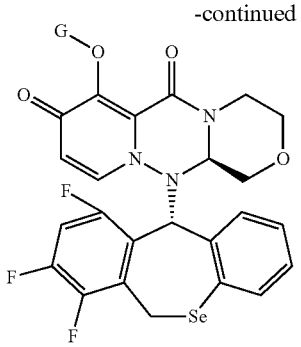

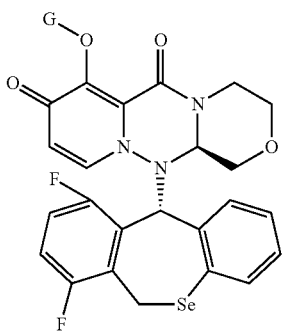

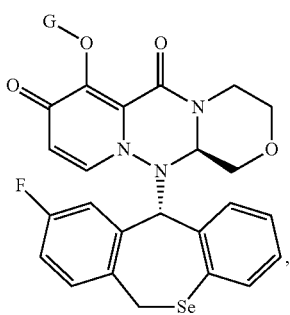

or a pharmaceutically acceptable salt, stereoisomer or solvate thereof.

In some embodiments, provided is a compound of Formula (I-3):

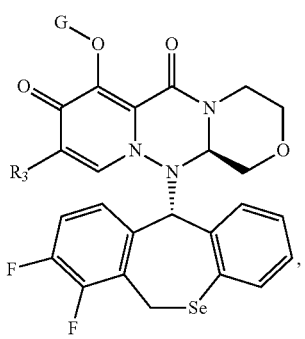

(I-3)

or a pharmaceutically acceptable salt, stereoisomer or solvate thereof, wherein G is as detailed herein for Formula (I).

In another aspect, the invention provides a compound of Formula (II):

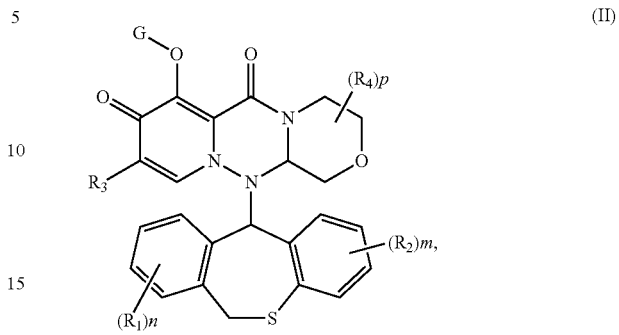

(II)

or a pharmaceutically acceptable salt, stereoisomer or solvate thereof, wherein:
each $R_1$ is independently selected from the group consisting of H and halo;
each $R_2$ is independently selected from the group consisting of H and halo;
$R_3$ is $P(O)Me_2$ or $P(O)Et_2$;
each $R_4$ is independently selected from the group consisting of $C_1$-$C_6$ alkyl and $C_3$-$C_6$ cycloalkyl, wherein any two of $R_4$ are optionally taken, together with the atoms to which they are attached, to form a $C_3$-$C_6$ cycloalkyl;
n and m are each independently 0, 1, 2, 3, or 4;
p is 0, 1, 2, or 3; and
G is H or is selected from the group consisting of C(O)R, C(O)OR, C(O)NR'R, C(R')$_2$—O—C(O)R, C(R')$_2$—O—C(O)OR, and C(R')$_2$—O—C(O)NR'R, wherein
each R is selected from the group consisting of $C_1$-$C_6$ alkyl, phenyl, pyridyl, $C_3$-$C_6$ cycloalkyl, and a 4-6 membered heterocyclic ring containing one or two heteroatoms selected from the group consisting of N, O and S as ring members, wherein the $C_1$-$C_6$ alkyl, phenyl, pyridyl, $C_3$-$C_6$ cycloalkyl, and 4-6 membered heterocyclic ring of R are independently optionally substituted with one or two substituents selected from the group consisting of H, halo, CN, OH, NH$_2$, $C_1$-$C_3$ alkyl, phenyl, $C_1$-$C_4$ alkoxy, $C_1$-$C_3$ haloalkyl, and $C_1$-$C_3$ haloalkoxy; and
each R' is independently selected from the group consisting of H and $C_1$-$C_3$ alkyl.

In some embodiments, provided is a compound of Formula (II-1):

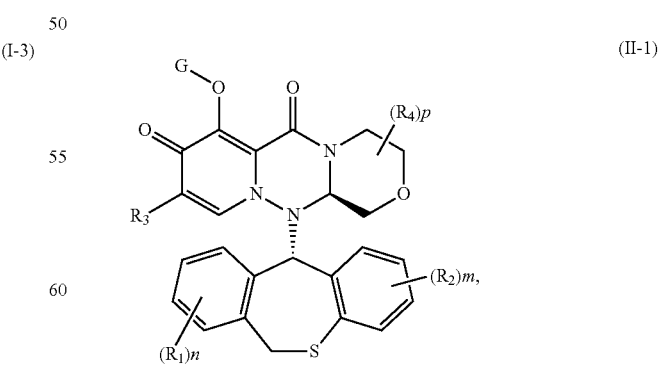

(II-1)

or a pharmaceutically acceptable salt, stereoisomer or solvate thereof, wherein $R_1$, $R_2$, $R_3$, $R_4$, m, n, p, and G are as detailed herein for Formula (II).

In some embodiments, provided is a compound of Formula (II-2):

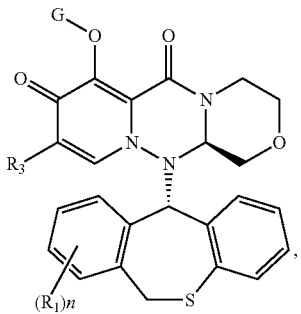
(II-2)

or a pharmaceutically acceptable salt, stereoisomer or solvate thereof, wherein $R_1$, n, $R_3$ and G are as detailed herein for Formula (II).

In some embodiments, provided is a compound of Formula (II-3):

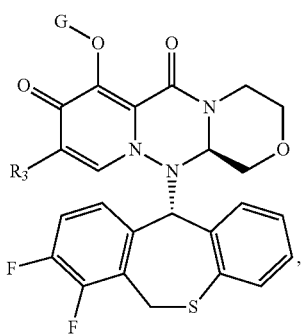
(II-3)

or a pharmaceutically acceptable salt, stereoisomer or solvate thereof, wherein $R_3$ and G are as detailed herein for Formula (II).

In some embodiments, the invention provides a compound of Formula (I), (I-1), (I-2), (I-3), (II), (II-1), (II-2), or (II-3), or a pharmaceutically acceptable salt, stereoisomer or solvate thereof, wherein G is hydrogen or is selected from the group consisting of:

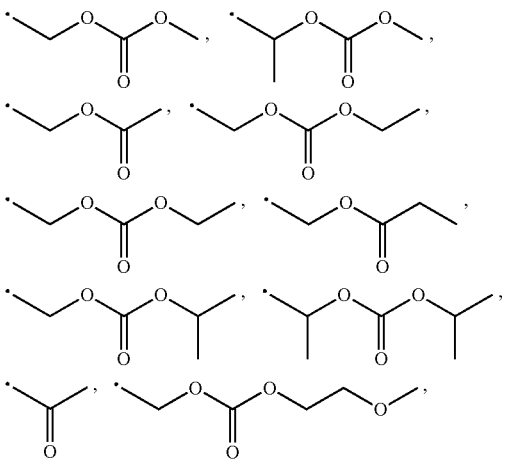

-continued

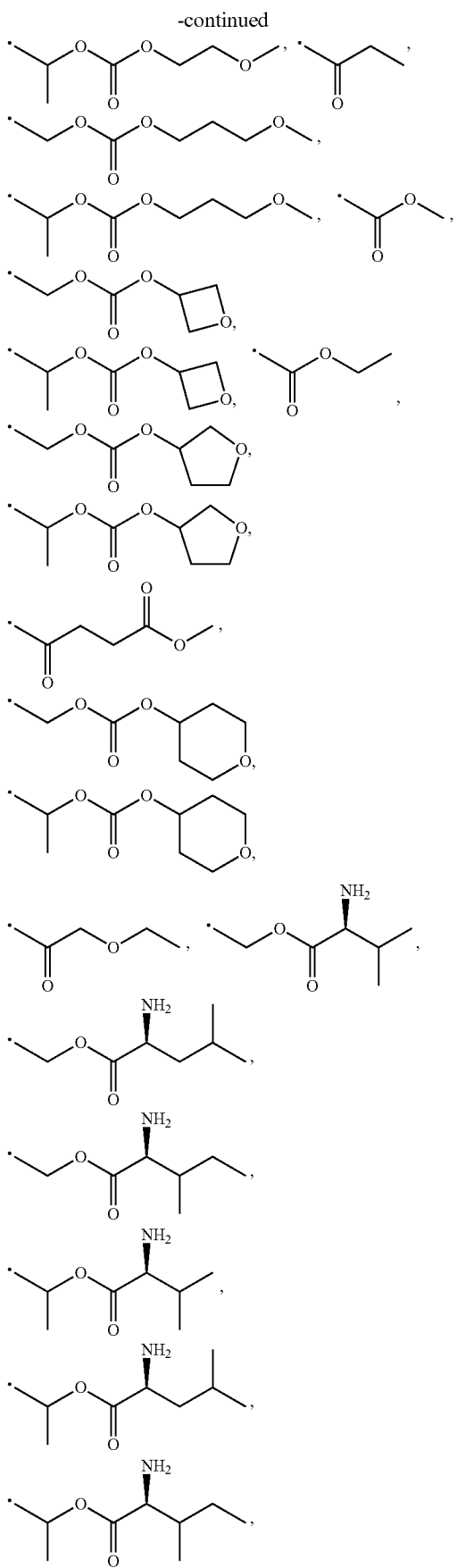

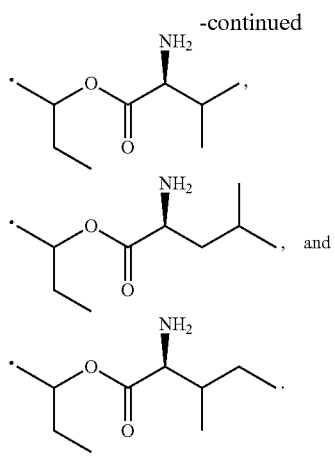

Pharmaceutical Compositions and Formulations

Pharmaceutical compositions of any of the compounds detailed herein or a pharmaceutically acceptable salt, stereoisomer or solvate thereof, are embraced by this disclosure. Thus, the present disclosure includes pharmaceutical compositions comprising a compound as detailed herein or a pharmaceutically acceptable salt, stereoisomer or solvate thereof, and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein or a pharmaceutically acceptable salt, stereoisomer or tautomer thereof, may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein or a pharmaceutically acceptable salt, stereoisomer or solvate thereof, and a pharmaceutically acceptable carrier. In another variation, methods of administering a compound are provided. The purified forms, pharmaceutical compositions and methods of administering the compounds are suitable for any compound or form thereof detailed herein.

A compound detailed herein or a pharmaceutically acceptable salt, stereoisomer or solvate thereof, may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a pharmaceutically acceptable salt, stereoisomer or solvate thereof, can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington's Pharmaceutical Sciences, Mack Publishing Company, Philadelphia, Pa., 20th ed. (2000), which is incorporated herein by reference.

Compounds or a pharmaceutically acceptable salt, stereoisomer or solvate thereof, as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein or a pharmaceutically acceptable salt, stereoisomer or solvate thereof, can be formulated in a tablet in any dosage form described, for example, a compound as described herein or a pharmaceutically acceptable salt thereof can be formulated as a 10 mg tablet.

Methods of Use and Uses

In addition to the compounds as disclosed herein, their pharmaceutically acceptable salts, stereoisomers, hydrates, solvates, and compositions and combinations comprising these compounds, the invention includes methods of using the same as further described herein.

The compounds of Formula (I) and (II), including all formulae (I-1), (I-2), (I-3), (II-1), (II-2), and (II-3), are inhibitors of the endonuclease function of influenza viruses as shown by the data provided herein, and they inhibit replication of influenza viruses. Accordingly, these compounds are useful to treat or prevent influenza virus infections in humans.

In another aspect, the invention provides pharmaceutical compositions comprising a compound of Formula (I) or (II), such as a compound of formula (I-1), (I-2), (I-3), (II-1), (II-2), and (II-3), administered with at least one pharmaceutically acceptable carrier or excipient, optionally administered with two or more pharmaceutically acceptable carriers or excipients. The compounds may be used as pharmaceutically acceptable salts and hydrates.

In another aspect, the invention provides a method to treat a subject infected with influenza A, B or C, which comprises administering to a subject in need of such treatment an effective amount of a compound of Formula (I) or (II), such as a compound of formula (I-1), (I-2), (I-3), (II-1), (II-2), or (II-3), or any subgenus or species thereof as described herein, or a pharmaceutical composition comprising such compound. The subject is a human, although the compounds and methods of the invention are suitable for treatment of other species that contract Influenza A, Influenza B, or influenza C, as well as other influenza viruses.

The compounds as disclosed herein, their pharmaceutically acceptable salts, stereoisomers, solvates thereof, exhibit the ability and drug properties to inhibit or prevent replication of influenza virus, as indicated by test data provided below, and are therefore indicated for therapy to inhibit replication of an influenza virus, particularly Influenza A, Influenza B or Influenza C. Accordingly, compounds of the invention are useful in the treatment of an infection caused by an influenza virus, particularly Influenza A, Influenza B or Influenza C, especially in human subjects having or at risk of contracting an influenza viral infection. For example, subjects having pre-existing conditions related to autoimmune or respiratory diseases that can be greatly exacerbated by an influenza infection may be treated with the methods or compounds of the invention before exhibiting symptoms of an influenza infection. In other aspects, the subject for treatment is one diagnosed as having symptoms consistent with an influenza infection. As a further aspect, the present invention provides the use of compounds as described herein as therapeutics. In particular, the compounds are suitable for use to treat a subject having or at particularly high risk for an influenza virus viral infection, especially Influenza A, Influenza B, or Influenza C.

In another aspect, the invention provides a method of treating a disease which is caused by an influenza virus, comprising administration of a therapeutically effective amount of a compound of formula (I) or (II) as described herein, such as a compound of formula (I-1), (I-2), (I-3), (II-1), (II-2), or (II-3), or a pharmaceutically acceptable salt, stereoisomer, solvate thereof, to a subject in need of such treatment. In some aspects, the compound or a pharmaceutically acceptable salt, stereoisomer, solvate thereof, is administered orally. In a further aspect, the disease is selected from Influenza A, Influenza B, and Influenza C. The method typically comprises administering an effective amount of a compound as described herein, or a pharmaceutical composition comprising an effective amount of such compound, to a subject in need of such treatment. The compound may be administered by any suitable method such as those described herein, and the administration may be repeated at intervals which may be selected by a physician. In some aspects, the compound or pharmaceutical composition is administered orally.

Thus, as a further aspect, the present invention provides the use of a compound of formula (I) or (II), such as a compound of formula (I-1), (I-2), (I-3), (II-1), (II-2), or (II-3), or a pharmaceutically acceptable salt, stereoisomer, solvate thereof, for the manufacture of a medicament. In a particular aspect, the medicament is for treatment of an influenza virus infection, especially Influenza A, Influenza B, or Influenza C.

The compound of the present invention may be administered either simultaneously with, or before or after, one or more therapeutic(s). The compound of the present invention may be administered separately, by the same or different route of administration, or together in the same pharmaceutical composition as the therapeutic(s). Suitable therapeutic(s) for use with the compounds of the invention include antivirals active on influenza viruses, such as neuraminidase inhibitors including oseltamivir, peramivir, zanamivir and laninamivir, laninamivir octanoate, and adamantanes such as amantadine and rimantadine. Additionally, the compounds can be combined with an M2 protein inhibitor, a polymerase inhibitor, a PB2 inhibitor, favipiravir, fludase, beraprost, Neugene®, ribavirin, Flu Mist Quadrivalent®, Fluarix® Quadrivalent, Fluzone® Quadrivalent, Flucelvax® and FluBlok®.

In one aspect, the invention provides a product comprising a compound of formula (I) or (II), such as a compound of formula (I-1), (I-2), (I-3), (II-1), (II-2), or (II-3), or a pharmaceutically acceptable salt, stereoisomer, solvate thereof, and at least another therapeutic as a combined preparation for simultaneous, separate or sequential use in therapy.

The invention also provides a therapeutic for use in a method of treating a viral infection caused by an influenza virus, particularly Influenza A, Influenza B or Influenza C, wherein the a therapeutic is administered with a compound of formula (I) or (II), such as a compound of formula (I-1), (I-2), (I-3), (II-1), (II-2), or (II-3), or a pharmaceutically acceptable salt, stereoisomer, solvate thereof.

The invention also provides the use of a compound of formula (I) or (II), such as a compound of formula (I-1), (I-2), (I-3), (II-1), (II-2), or (II-3), or a pharmaceutically acceptable salt, stereoisomer, solvate thereof, for treating a viral infection caused by an influenza virus, particularly influenza, such as Influenza A, Influenza B or Influenza C, wherein the patient has previously (e.g., within 24 hours) been treated with another therapeutic agent. The invention also provides the use of another therapeutic agent for treating a viral infection caused by an influenza virus, particularly Influenza A, Influenza B or Influenza C, wherein the patient has previously (e.g., within 24 hours) been treated with a compound of formula (I) or (II), or a pharmaceutically acceptable salt, stereoisomer, solvate thereof.

In one aspect, the combination therapeutics is selected from antivirals purported to be useful for treating infections caused by influenza viruses, such as neuraminidase inhibitors including oseltamivir, peramivir, zanamivir and laninamivir, and adamantanes such as amantadine and rimantadine.

The pharmaceutical composition or combination of the present invention in human is dependent on the body weight, age and individual condition, the disorder or disease or the severity thereof being treated. The effective dose is determined by a physician or clinician to prevent, treat or inhibit the progress of the disorder or disease.

The above cited dosage properties are demonstrable in vitro and in vivo tests using advantageously mammals, such as mice, rats, dogs, monkeys or isolated organs, tissues and preparations thereof. The invention further includes processes to make the compounds of Formulae (I) and (II), such as a compound of formula (I-1), (I-2), (I-3), (II-1), (II-2), or (II-3), as disclosed herein.

In the practice of the method of the present invention, a therapeutically effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

The dose of a compound administered to an individual (such as a human) may vary with the particular compound or salt thereof, the method of administration, and the particular disease being treated. The effective amount of the compound may, in one aspect, be a daily dose of between about 0.01 and about 100 mg/kg of body weight; in some embodiments, from about 0.05 to 10.0 mg/kg of body weight, and in some embodiments, from about 0.10 to 1.4 mg/kg of body weight. For administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. Effective amounts or doses of the compounds of the invention may be ascertained by routine methods, such as modeling, dose escalation, or clinical trials, taking into account factors, e.g., the mode or route of administration or drug delivery, the pharmacokinetics of the agent, the severity and course of the disease to be treated, the subject's health status, condition, and weight. An exemplary dose is in the range of about from about 0.1 mg to 10 g daily. For example, an exemplary dosage range for oral administration is from about 5 mg to about 500 mg per day, and an exemplary intravenous administration dosage is from about 5 mg to about 500 mg per day, each depending upon the pharmacokinetics.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Articles of Manufacture and Kits

The present disclosure further provides articles of manufacture comprising a compound of the disclosure or a salt thereof, composition, and unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the disclosure, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of disease described herein.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

In some embodiments, the invention provides selenium and/or phosphine containing compounds.

Among the provided embodiments are:

Embodiment 1. A compound of Formula (A):

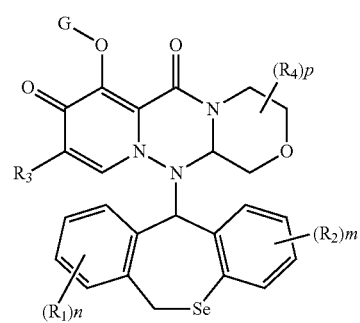

Formula A or a pharmaceutically acceptable salt or solvate thereof, wherein:

$R_1$ is independently selected from H and/or fluoro, n=0-4;
$R_2$ is independently selected from H and/or fluoro, n=0-4;
$R_3$ is selected from H, F, Cl, Br, Me, CN, and P(O)Me2;
$R_4$ is independently selected from Me and/or fluoro, p=0-3;
G is H or is a group selected from C(O)R, C(O)OR, C(O)NR'R, C(R')$_2$—O—C(O)R, C(R')2-OC(O)OR, and C(R')$_2$—O—C(O)NR, where each R is a group selected from C1-C6 alkyl, phenyl, pyridyl, C3-C6 cycloalkyl, and a 4-6 membered heterocyclic ring containing one or two heteroatoms selected from N, O and S as ring members; and each R is optionally substituted with one or two groups selected from H, halo, CN, OH, amino, C1-C3 alkyl, phenyl, C1-C4 alkoxy, C1-C3 haloalkyl, and C1-C3 haloalkoxy; and each R' is independently selected from the group consisting of H and C₁-C₃ alkyl.

Embodiment 2. The compound of embodiment 1, wherein G=H, or a pharmaceutically acceptable salt or solvate thereof.

Embodiment 3. The compound of embodiment 1, wherein G=C(O)R, C(O)OR, C(O)NR'R, C(R')₂—O—C(O)R, C(R')₂—O—C(O)OR, and C(R')₂—O—C(O)NR, where each R is a group selected from C1-C6 alkyl, phenyl, pyridyl, C3-C6 cycloalkyl, and a 4-6 membered heterocyclic ring containing one or two heteroatoms selected from N, O and S as ring members; and each R is optionally substituted with one or two groups selected from H, halo, CN, OH, amino, C1-C3 alkyl, phenyl, C1-C4 alkoxy, C1-C3 haloalkyl, and C1-C3 haloalkoxy; and each R' is independently selected from the group consisting of H and C1-C3 alkyl, or a pharmaceutically acceptable salt or solvate thereof.

Embodiment 4. The compound of embodiment 1, wherein G=C(O)R, C(O)OR, C(R')₂—O—C(O)R, and C(R')₂—O—C(O)OR, where each R is a group selected from C1-C6 alkyl, phenyl, pyridyl, C3-C6 cycloalkyl, and a 4-6 membered heterocyclic ring containing one or two heteroatoms selected from N, O and S as ring members; and each R is optionally substituted with one or two groups selected from H, halo, CN, OH, amino, C1-C3 alkyl, phenyl, C1-C4 alkoxy, C1-C3 haloalkyl, and C1-C3 haloalkoxy; and each R' is independently selected from the group consisting of H and C1-C3 alkyl, or a pharmaceutically acceptable salt or solvate thereof.

Embodiment 5. The compound of embodiment 1, wherein G=C(O)R, C(O)OR, CH₂—O—C(O)R, and CH₂—O—C(O)OR, where each R is a group selected from C1-C5 alkyl and each R is optionally substituted with one group selected from H, halo, CN, OH, amino, or a pharmaceutically acceptable salt or solvate thereof.

Embodiment 6. The compound of embodiment 1, which is of the formula B:

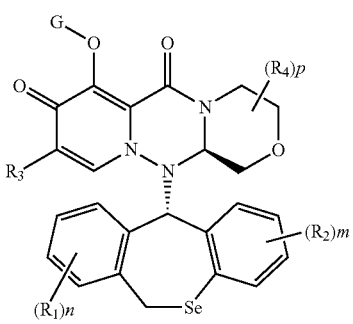

Formula B or a pharmaceutically acceptable salt or solvate thereof.

Embodiment 7. The compound of embodiment 6, wherein R1 is independently selected from H and/or fluoro, n=0-4; R2 is independently selected from H and/or fluoro, n=0-4; R3 is selected from H, F, Cl, Br, Me, CN, and P(O)Me2; G is H or a group selected from C(O)R, C(O)OR, C(O)NR'R, C(R')₂—O—C(O)R, C(R')₂—O—C(O)OR, and C(R')₂—O—C(O)NR, where each R is a group selected from C1-C6 alkyl, phenyl, pyridyl, C3-C6 cycloalkyl, and a 4-6 membered heterocyclic ring containing one or two heteroatoms selected from N, O and S as ring members; and each R is optionally substituted with one or two groups selected from H, halo, CN, OH, amino, C1-C3 alkyl, phenyl, C1-C4 alkoxy, C1-C3 haloalkyl, and C1-C3 haloalkoxy; and each R' is independently selected from the group consisting of H and C1-C3 alkyl, or a pharmaceutically acceptable salt or solvate thereof.

Embodiment 8. The compound of embodiment 1, which is of the formula C:

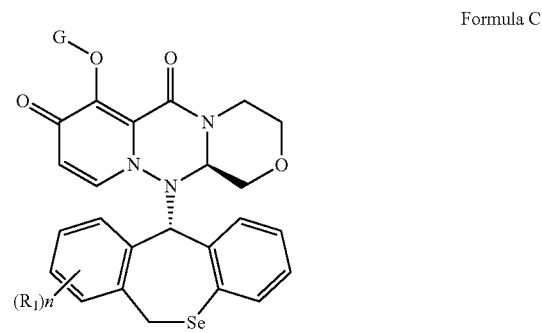

Formula C

R1 is independently selected from H and/or fluoro, n=0-4; G is H or a group selected from C(O)R, C(O)OR, C(O)NR'R, C(R')₂—O—C(O)R, C(R')₂—O—C(O)OR, and C(R')₂—O—C(O)NR, where each R is a group selected from C1-C6 alkyl, phenyl, pyridyl, C3-C6 cycloalkyl, and a 4-6 membered heterocyclic ring containing one or two heteroatoms selected from N, O and S as ring members; and each R is optionally substituted with one or two groups selected from H, halo, CN, OH, amino, C1-C3 alkyl, phenyl, C1-C4 alkoxy, C1-C3 haloalkyl, and C1-C3 haloalkoxy; and each R' is independently selected from the group consisting of H and C1-C3 alkyl, or a pharmaceutically acceptable salt or solvate thereof.

Embodiment 9. The compound of embodiment 8, which is of the formula D:

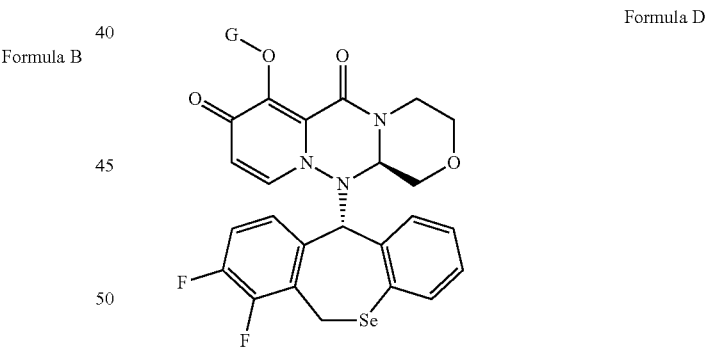

Formula D

G is H or a group selected from C(O)R, C(O)OR, C(O)NR'R, C(R')₂—O—C(O)R, C(R')₂—O—C(O)OR, and C(R')₂—O—C(O)NR, where each R is a group selected from C1-C6 alkyl, phenyl, pyridyl, C3-C6 cycloalkyl, and a 4-6 membered heterocyclic ring containing one or two heteroatoms selected from N, O and S as ring members; and each R is optionally substituted with one or two groups selected from H, halo, CN, OH, amino, C1-C3 alkyl, phenyl, C1-C4 alkoxy, C1-C3 haloalkyl, and C1-C3 haloalkoxy; and each R' is independently selected from the group consisting of H and C1-C3 alkyl, or a pharmaceutically acceptable salt or solvate thereof.

Embodiment 10. The compound of embodiment 9, wherein G=C(O)R, C(O)OR, CH₂—O—C(O)R, and CH₂—

O—C(O)OR, where each R is a group selected from C1-C5 alkyl and each R is optionally substituted with one group selected from H, halo, CN, OH, amino, or a pharmaceutically acceptable salt or solvate thereof.

Embodiment 11. A pharmaceutical composition comprising a compound of embodiment 1, or a pharmaceutically acceptable salt and solvate thereof, and one or more pharmaceutically acceptable carriers.

Embodiment 12. A method of treating influenza, comprising administering to a subject in need thereof a therapeutically effective amount of a compound of embodiment 1, or a pharmaceutically acceptable salt and solvate thereof.

The invention can be further understood by reference to the following examples, which are provided by way of illustration and are not meant to be limiting.

EXAMPLES

Synthetic Examples

Reagents and solvates used below can be obtained from commercial sources. $^1$H-NMR spectra were recorded on Varian III plus 300 MHz and TMS was used as an internal standard. Significant peaks are tabulated in the order: multiplicity (s, singlet; d, doublet; t, triplet; q, quartet; m, multiplet; br s, broad singlet), coupling constant(s) in Hertz (Hz) and number of protons. Mass spectrometry results are reported as the ratio of mass over charge, followed by the relative abundance of each ion in parentheses Electrospray ionization (ESI) mass spectrometry analysis was conducted on a quadrupole Mass Spectrometer on Agilent LC/MSD 1200 Series (Column: Welchrom XB-C18 (50×4.6 mm, 5 μm); T=30° C.; flow rate=1.5 ml/min. detected wavelength: 214 nm.

The terms "solvent", "inert organic solvent", or "inert solvent" refer to a solvent inert under the conditions of the reaction being described in conjunction therewith including, for example, benzene, toluene, acetonitrile, tetrahydrofuran ("THF"), dimethylformamide ("DMF"), ethyl acetate (EA or EtOAc), dichloromethane (DCM), diethyl ether, methanol, pyridine, formic acid (FA) and the like. Unless specified to the contrary, the solvates used in the reactions of the present invention are inert organic solvates, and the reactions are carried out under an inert gas, preferably nitrogen and argon.

Example 1

Synthesis of 12-(7,8-Difluoro-6,11-Dihydrodibenzo[b,e]Selenepin-11yl)-7-Hydroxy-3,4,12,12a-Tetrahydro-1H-[1,4]Oxazino[3,4-c]Pyrido[2,1-f][1,2,4]Triazine-6,8-Dione (A-1)

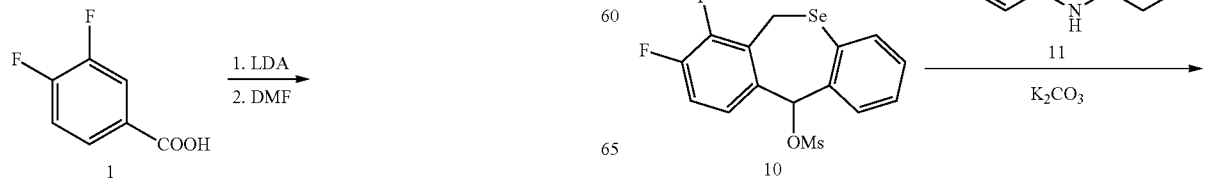

-continued

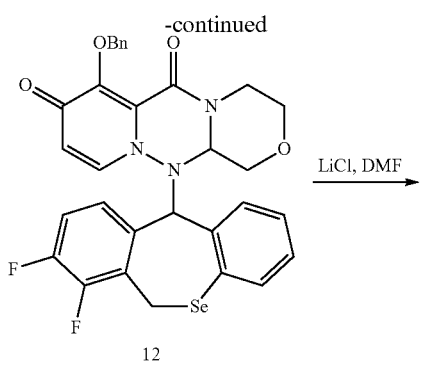
12

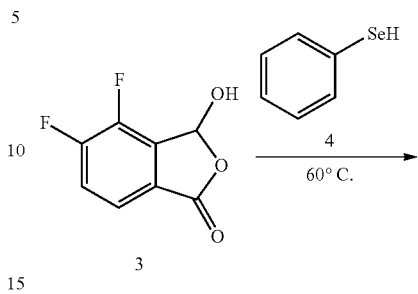

A-1

Synthesis of
4,5-Difluoro-3-Hydroxyisobenzofuran-1(3H)-One
(3)

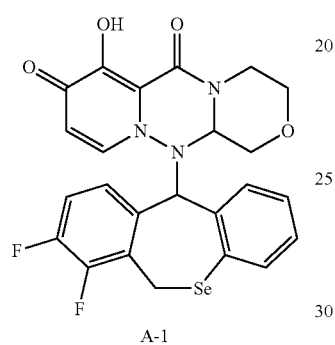

To a solution of LDA (4.8 g, 0.045 mol) in THF (15 mL) was slowly added a solution of 3,4-difluorobenzoic acid (3 g, 0.019 mol) in THF (5 mL) at −40° C. The reaction solution was stirred at −40° C. for 1 hour, and DMF (3.45 g, 0.047 mol) was added slowly, 6 mol/L hydrochloric acid in water (20 mL) was added to the reaction mixture, and then the organic layer and the aqueous layer were separated. The obtained aqueous layer was extracted with ethyl acetate (30 mL). The organic layers were combined and concentrated to obtain crude compound 3 (3.55 g), which was used directly in the next step without further purification. MS Calcd: 186; MS Found: 185 ([M−H]⁻).

Synthesis of 4,5-Difluoro-3-(Phenylselanyl)Isobenzofuran-1(3H)-One (5)

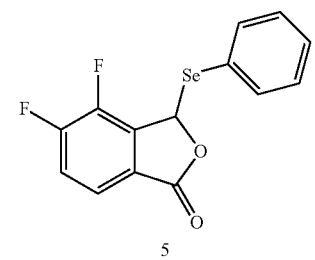

5

To a solution of compound 3 (3.5 g, 19 mmol) in toluene (20 mL) was added compound 4 (2 g, 12.5 mmol) and D-camphorsulfonic acid (0.7 g, 3 mmol). The mixture was stirred at 60° C. overnight and then cooled to 5° C. A sodium hydroxide aqueous solution (7 mL, 2 M) was added to the reaction solution. The temperature was raised to 25° C. The reaction solution was extracted with toluene (30 mL). The obtained organic layers were concentrated under reduced pressure, purified by flash column chromatography on silica gel (PE: EA=5:1) to afford compound 5 (3 g, yield 50%) as a white solid. $^1$H-NMR (400 MHz, CDCl$_3$): δ7.48-7.46 (d, J=6.8 Hz, 2H), 7.42-7.34 (m, 1H), 7.30-7.16 (m, 4H), 6.97 (s, 1H). MS Calcd: 326; MS Found: 325 ([M−H]⁻).

Synthesis of
3,4-Difluoro-2-((Phenylselanyl)Methyl)Benzoic
Acid (7)

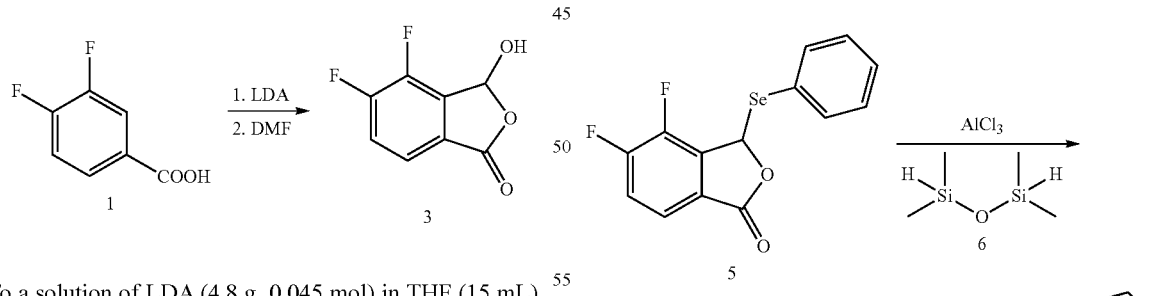

A solution of aluminum chloride (0.8 g, 414 mmol) in toluene (20 mL) was stirred at 0° C. Then compound 6 (0.8 g, 6 mmol) in toluene (3 mL) was added dropwise to the reaction solution, and the temperature was raised to 25° C. The solution of compound 5 (1.5 g, 4.6 mmol) in toluene (5 mL) was slowly added to the reaction solution, and the mixture was stirred at 25° C. for 2.5 hours. After addition of 15% aqueous sulfuric acid (5 mL), the resulted reaction mixture was stirred and the organic layer was separated and concentrated under reduced pressure to afford compound 7 (2 g) as a yellow solid, which was used directly in the next step without further purification. MS Calcd: 328; MS Found: 327 ([M−H]−).

Synthesis of 7,8-Difluorodibenzo[b,e]Selenepin-11 (6H)-One (8)

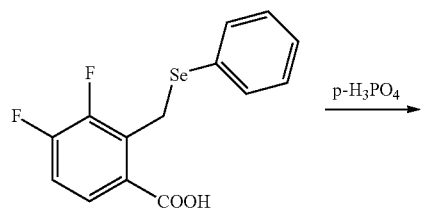

7 p-H3PO4

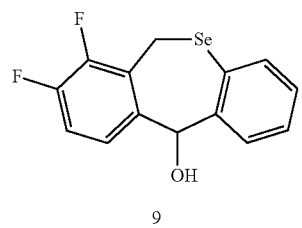

8

Polyphosphoric acid (20 g) was stirred at 80° C. and compound 7 (2 g, 4.6 mmol) was added thereto. The temperature was raised to 120° C. and the reaction was kept for 3 hours. The reaction solution was cooled to 80° C., and water (10 mL) was added slowly. The reaction solution was then further cooled to 30° C., and water (20 mL) was added. The resulted mixture was extracted with ethyl acetate (30 mL). The organic layer was distilled off under reduced pressure and then purified by flash column chromatography on silica gel (PE: EA=50:1) to afford compound 8 (560 mg, yield 36%) as a brown solid. 1H-NMR (400 MHz, CDCl3): δ8.09 8.07 (m, 1H), 7.40-7.18 (m, 3H), 7.00 6.97 (m, 2H), 4.04 (s, 2H); MS Calcd: 310; MS Found: 311 ([M+14]+).

Synthesis of 7,8-Difluoro-6,11-Dihydrodibenzo[b,e] Selenepin-11-Ol (9)

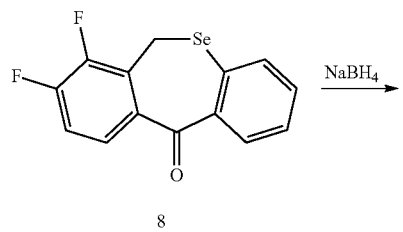

8

NaBH4

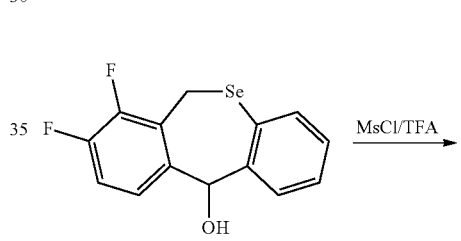

9

To a solution of compound 8 (560 mg, 1.8 mmol) in 2-propanol (5 mL) and H2O (1.0 mL) was added NaOH (2 mg) and NaBH4 (24 mg, 0.65 mmol). The reaction mixture was stirred at 40° C. for 2 hours and cooled to 25° C. Water (10 mL) was added to the reaction mixture, and water and HCl were added to adjust the reaction mixture to pH=6~7. The resulted mixture was extracted with EA (30 mL) and purified by flash column chromatography on silica gel (PE: EA=10:0~10:1) to afford compound 9 (460 mg, yield 80%) as a yellow solid. 1H-NMR (300 MHz, CDCl3): δ7.68-7.66 (d, J=7.5 Hz, 1H), 7.29-7.22 (m, 3H), 7.15-7.05 (m, 2H), 6.21-6.21 (d, J=1.8 Hz, 1H), 4.48 (s, 2H), 2.49-2.48 (d, J=2.7 Hz, 1H); MS Calcd: 312; MS Found: 311 ([M−H]−).

Synthesis of 7,8-Difluoro-6,11-Dihydrodibenzo[b,e] Selenepin-11-yl Methanesulfonate (10)

9

MsCl/TFA

10

To a solution of compound 9 (200 mg, 0.64 mmol) in DCM (15 mL) was added TEA (194 mg, 1.9 mmol) at 0° C., then MsCl (111 mg, 0.96 mmol) was added under N2 atmosphere. The reaction was stirred at 0° C. for 2 hours. The reaction was diluted with DCM (20 mL), washed with HCl (1N, 10 ml*3), brine. The organic phase was dried over Na2SO4, filtered and removed solvent under reduce pressure to afford crude compound 10 (175 mg), as a yellow oil, which was used directly in next step without further purification.

Synthesis of 7-(Benzyloxy)-12-(7,8-Difluoro-6,11-Dihydrodibenzo[b,e]Selenepin-11-yl)-3,4,12,12a-Tetrahydro-1H-[1,4]Oxazino[3,4-c]Pyrido[2,1-f][1,2,4]Triazine-6,8-Dione (12)

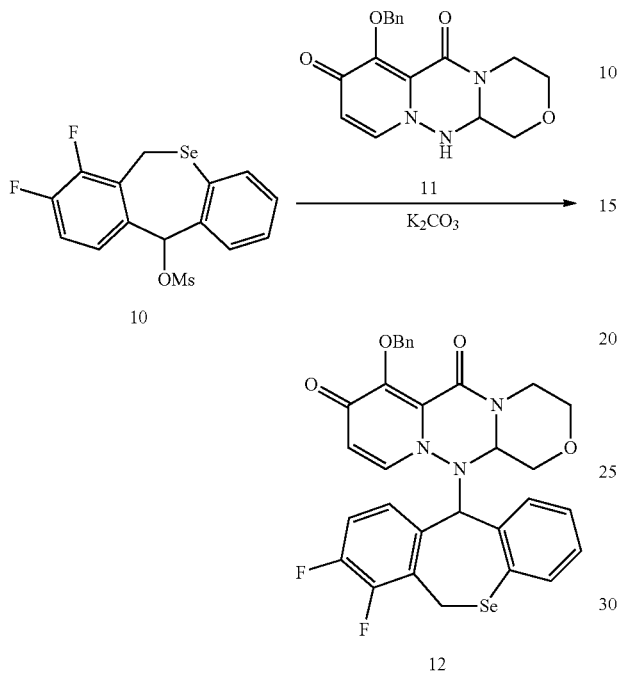

To a suspension of compound 10 (130 mg, 0.397 mmol) in MeCN (10 mL) was added K₂CO₃ (82 mg, 0.596 mmol). After stirred at r.t. for 1 hour, the crude compound 11 (232 mg, 0.596 mmol, made in a similar manner as described in JP5971830B1) was added, then the reaction mixture was stirred at r.t. overnight. The reaction was diluted with EA (30 mL), washed with water and brine, and concentrated before being purified by prep-HPLC to afford compound 12 (85 mg, yield 34.4%) as a yellow solid. MS Calcd: 621; MS Found: 622 ([M+H]⁺).

Synthesis of 12-(7,8-Difluoro-6,11-Dihydrodibenzo[b,e]Selenepin-11-yl)-7-Hydroxy-3,4,12,12a-Tetrahydro-1H-[1,4]Oxazino[3,4-c]Pyrido[2,1-f][1,2,4]Triazine-6,8-Dione (A-1)

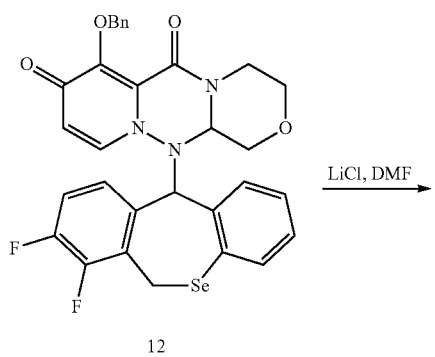

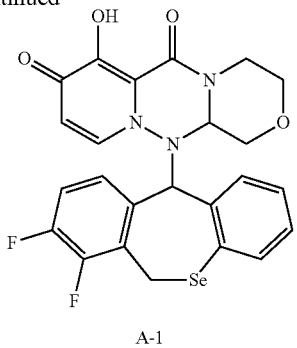

To a solution of compound 12 (50 mg, 0.08 mmol) in NMP (1.5 mL) was added LiCl (34 mg, 0.8 mmol) at 80° C. overnight. The reaction was cooled to room temperature and purified by Prep-HPLC to afford two fractions of A-1 (P1, 7 mg and P2, 7 mg) as a light yellow solid. A-1-P1 and A-1-P2 each are both a mixture of two diastereomers.

A-1-P1: ¹1-I-NMR (400 MHz, CDCl₃): δ7.31-7.22 (m, 2H), 7.14-6.98 (m, 3H), 6.93-6.89 (m, 1H), 6.72-6.70 (d, J=7.6 Hz, 1H), 6.08-6.06 (d, J=7.6 Hz, 1H), 5.34 (s, 1H), 5.18-5.14 (m, 1H), 4.71-4.66 (m, 2H), 4.10-4.03 (m, 2H), 3.86-3.82 (m, 1H), 3.66-3.60 (m, 1H), 3.52-3.46 (m, 1H), 3.07-3.00 (m, 1H). LCMS [mobile phase: from 95% water (0.1% TFA) and 5% acetonitrile to 5% water (0.1% TFA) and 95% acetonitrile in 6 min, finally under these conditions for 0.5 min.] purity is >95%, Rt=3.604 min; MS Calcd.: 531; MS Found: 532 ([M+1]+).

A-1-P2: ¹1-1-NMR (400 MHz, CDCl₃): δ7.36-7.18 (m, 4H), 6.93-6.89 (m, 2H), 6.64-6.61 (m, 1H), 6.20-6.17 (d, J=8 Hz, 1H), 5.45-5.41(m, 1H), 5.17 (s, 1H), 4.57-4.51 (m, 2H), 4.13-4.08 (m, 2H), 3.80-3.76 (m, 1H), 3.61-3.56 (m, 1H), 3.47-3.42 (m, 1H), 2.77-2.72 (m, 1H). LCMS [mobile phase: from 70% water (0.1% TFA) and 30% acetonitrile to 30% water (0.1% TFA) and 70% acetonitrile in 6 min, finally under these conditions for 0.5 min.] purity is >96%, Rt=3.276 min; MS Calcd.: 531; MS Found: 532 ([M+1]+).

A mixture of stereoisomers (including, for example, a pair of enantiomers or a mixture of diastereomers) may be separated by any suitable method, including, but not limited to, chiral HPLC. When a mixture of stereoisomers is separated by HPLC, it is to be appreciated that the resultant individual stereoisomers or mixtures will be assigned sequential labels (e.g., P1, P2, etc.), the order of which implies the order in which the isomers eluted from the HPLC column. In this Example, when the mixture of A-1 is separated by HPLC, it is to be appreciated that the first-eluting mixture of disasteromers is labeled "P1," and the second-eluting mixture of disasteromers is labeled "P2." The absolute stereochemistry for "P1" and "P2" may be obtained by known methods.

Synthesis of compounds A-2 to A-9

Compounds A-2 to A-9 are synthesized in a similar manner as A-1 from the corresponding starting materials substituted 2-formylbenzoic acids.

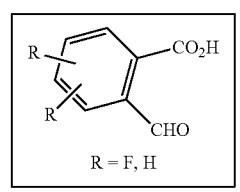

R = F, H

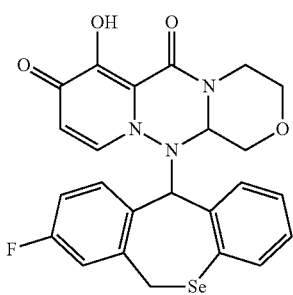 A-2

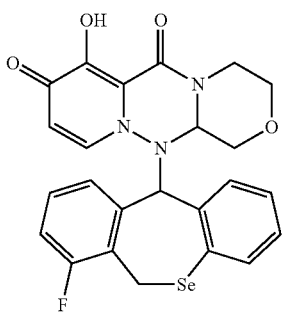 A-3

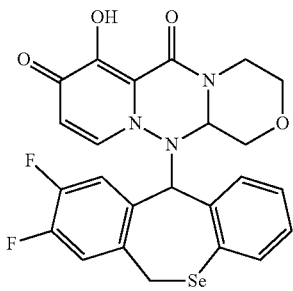 A-4

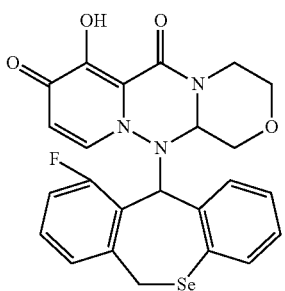 A-5

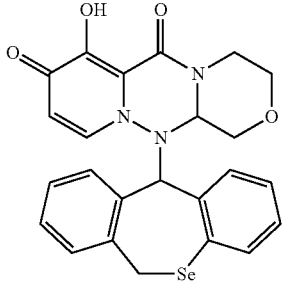 A-6

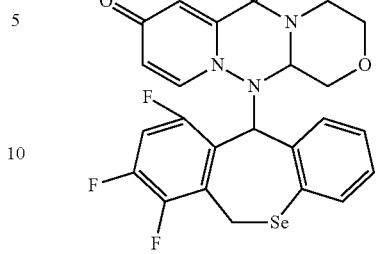 A-7

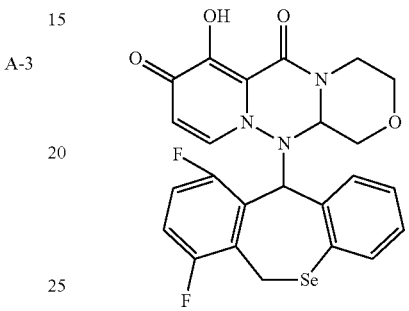 A-8

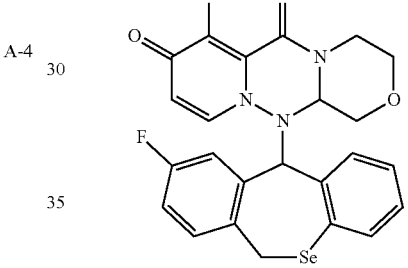 A-9

In some embodiments, provided herein is a compound selected from the group consisting of:

8-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-2), 7-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-3), 8,9-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-4), 10-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-5), 6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-6), 7,8,10-trifluoro-6,11-dihydrodibenzo[b,e]selenepin-11-yl)-3,4,12,12a-tetrahydro-1H-[1,4]oxazino[3,4-c]pyrido[2,1-f][1,2,4]triazine-6,8-dione (A-7), 7,10-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-8), and 9-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-9).

Example 2

Synthesis of (R)-12-((S)-7,8-Difluoro-6,11-Dihydrodibenzo[b,e]Selenepin-11-yl)-7-Hydroxy-3,4,12,12a-Tetrahydro-1H-[1,4]Oxazino[3,4-c]Pyrido[2,1-f][1,2,4]Triazine-6,8-Dione (B-1)

B-1

Synthesis of (R)-7-(benzyloxy)-3,4,12,12a-tetrahydro-1H-[1,4]oxazino[3,4-c]pyrido[2,1-f][1,2,4]triazine-6,8-dione (11-R)

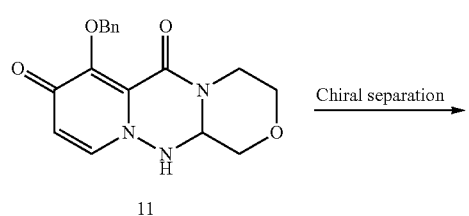

11

Chiral separation →

11-R

Compound 11 (7.0 g, 21.4 mmol) was separated with chiral HPLC: 60-40% CO$_2$, solvent (MeOH), column (IA). Collect peak 1 to obtained 11-R (3.2 g, yield 45.7%).

Synthesis of (R)-7-(Hexyloxy)-3,4,12,12a-Tetrahydro-1H-[1,4]Oxazino[3,4-c]Pyrido[2,1-f][1,2,4]Triazine-6,8-Dione (13)

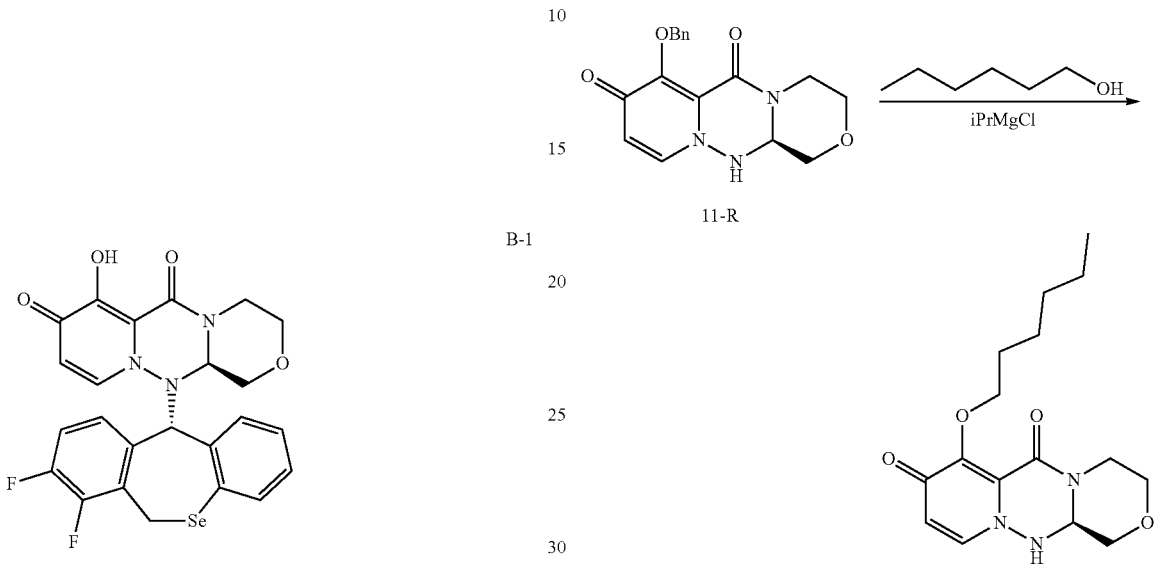

13

To a solution of hexan-1-ol (5.5 g, 55 mmol) in THF (12 mL) was added i-PrMgCl (3.7 mL, 3.7 mmol), and the mixture was stirred at room temperature for 0.5 h. The solution was added to a suspension of compound 11-R (3.0 g, 9.17 mmol) in hexan-1-ol (5.5 g, 55 mmol), then stirred at room temperature for 24 h. The reaction was quenched by HCl (1N) to pH7, extracted with EtOAc (20 mL*3) and purified by flash column chromatography on silica gel (DCM:MeOH=10:1) to afford compound 13 (2.3 g, yield 78.2%) as a white solid, which was used in next step without further purification. MS Calcd: 321; MS Found: 322 ([M+H]$^+$).

The above description of synthesis of compound 13 from 11-R can be catalyzed by other reagents such as Li salts or K salts other than iPrMgCl. For example, LDA (lithium diisopropylamide), alkyoxy Li salts or K salts, LHMDS (lithium bis(trimethylsilyl)amide), or KHMDS (potassium bis(trimethylsilyl)amide) were applied to the conversion of compound 11-R to compound 13.

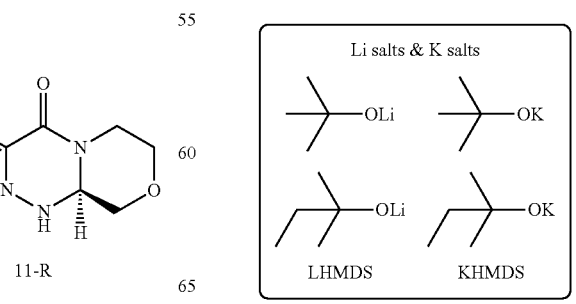

33

Synthesis of (R)-12-((S)-7,8-difluoro-6,11-dihydrodibenzo[b,e]selenepin-11-yl)-7-(hexyloxy)-3,4,12,12a-tetrahydro-1H-[1,4]oxazino[3,4-c]pyrido[2,1-f][1,2,4]triazine-6,8-dione (14)

34

Synthesis of (R)-12-((S)-7,8-Difluoro-6,11-Dihydrodibenzo[b,e]Selenepin-11-yl)-7-Hydroxy-3,4,12,12a-Tetrahydro-1H-[1,4]Oxazino[3,4-c]Pyrido[2,1-f][1,2,4]Triazine-6,8-Dione (B-1)

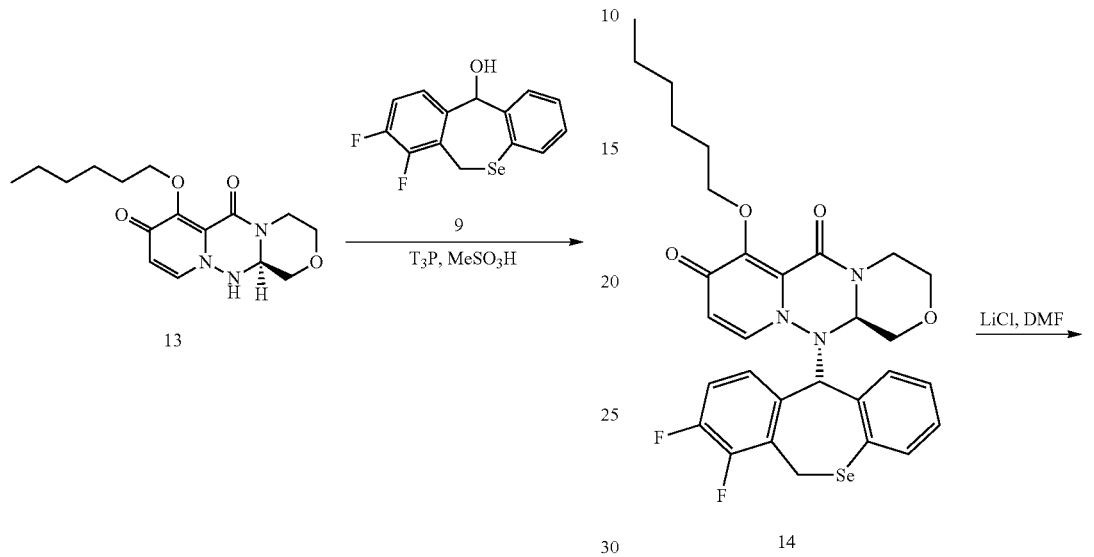

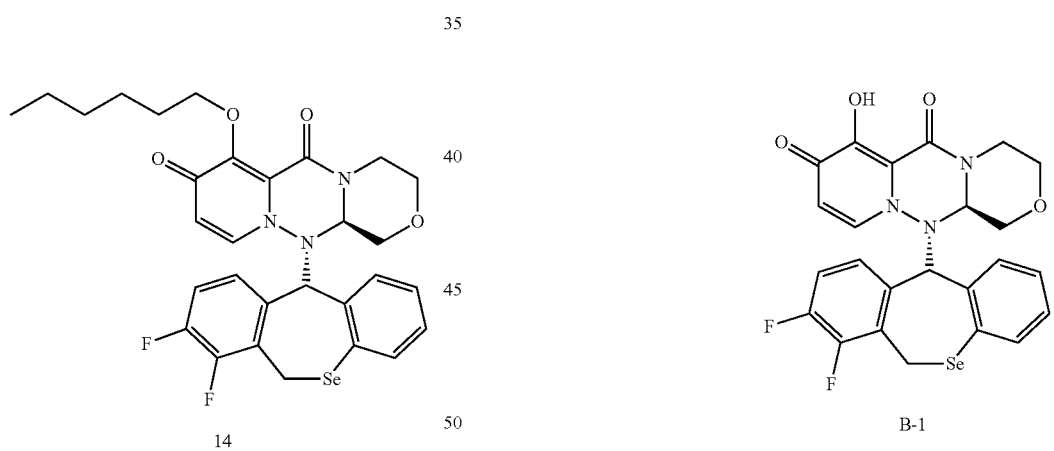

To a suspension of compound 13 (1.7 g, 5.29 mmol) in EA (12 mL) was added hexane (3.5 mL), compound 9 (1.65 g, 5.3 mmol), T$_3$P (6.75 g, 10.6 mmol), MeSO$_3$H (1.7 g, 17.7 mmol). The reaction was stirred at 60° C. overnight, and LCMS showed that most of compound 13 was converted to compound 14. The reaction mixture was cooled down to r.t, diluted with EA (30 mL), added 20% NaOH to pH>8, extracted with EA, dried over Na$_2$SO$_4$, concentrated and purified by Prep-HPLC (0.1% TFA) to obtain compound 14 (1.06 g, yield 32.6%) as an off-white solid. MS Calcd: 615; MS Found: 616 ([M+H]$_+$).

To a suspension of compound 14 (1.06 g, 1.72 mmol) in NMP (5 mL) was added LiCl (724 mg, 17.2 mmol), then the reaction mixture was stirred at 90° C. for 24 h. The reaction was purified by Prep-HPLC (0.1% TFA) to afford compound B-1 (367 mg, 86.3%) as a white solid. $^1$-NMR (400 MHz, DMSO-d6): δ7.41-7.30 (m, 2H), 7.26-7.19 (m, 2H), 7.13-7.06 (m, 2H), 6.92-6.88 (m, 1H), 5.81 (s, 1H), 5.61-5.59 (d, J=7.6 Hz, 1H), 5.31-5.27 (dd, J=2 Hz and 12.4 Hz, 1H), 4.61-4.58 (m, 1H), 4.45-4.42 (m, 1H), 4.13-4.10 (d, J=12.8 Hz, 1H), 4.04-4.01 (m, 1H), 3.70-3.64 (m, 2H), 3.46-3.40 (m, 1H), 3.09-3.02 (m, 1H). LCMS [mobile phase: from 80% water (0.1% TFA) and 20% acetonitrile to 30% water (0.1% TFA) and 70% acetonitrile in 6 min, finally under these conditions for 0.5 min.] purity is >98%, Rt=3.793 min; MS Calcd.: 531; MS Found: 532 ([M+1]$^+$).

Synthesis of compounds B-2 to B-9

Compounds B-2 to B-9 are obtained in a similar manner as compound B-1.

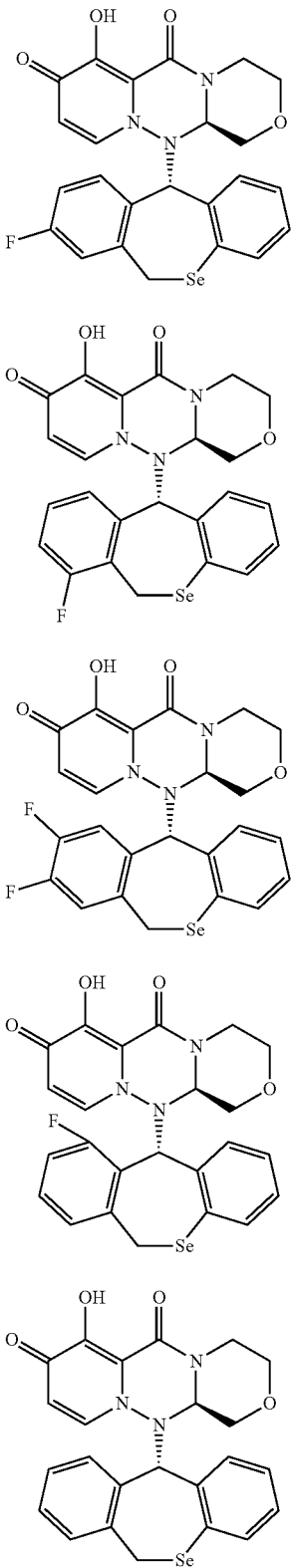

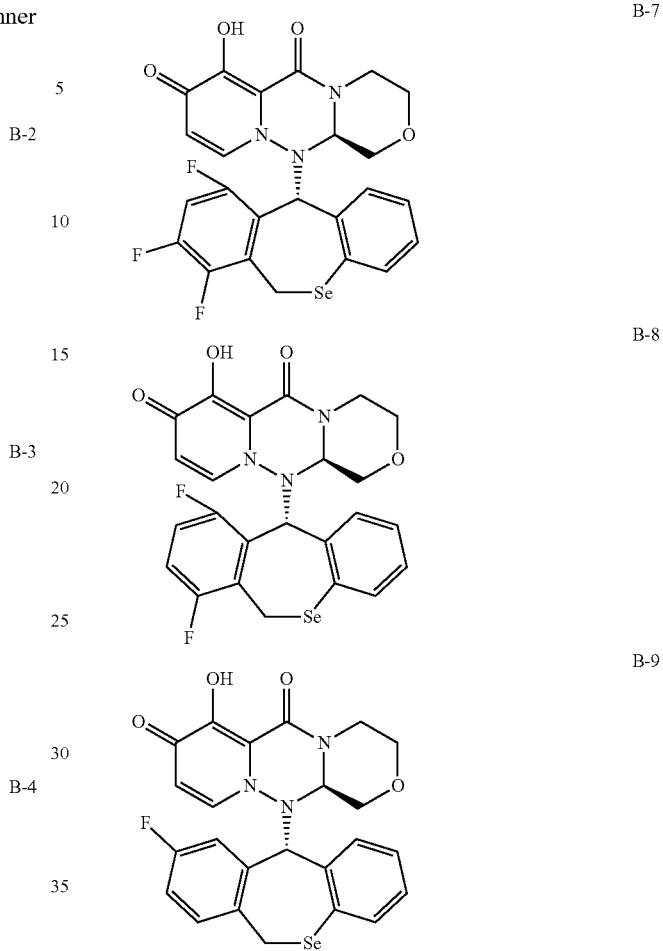

In some embodiments, provided herein is a compound selected from the group consisting of:

(R)-12-((S)-8-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-2), (R)-12-((S)-7-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-3), (R)-12-((S)-8,9-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-4), (R)-12-((S)-10-fluoro-6,11-dihydrodibenzo[b,e]selenepin-11-yl)-7-hydroxy-3,4,12,12a-tetrahydro-1H[1,4]oxazino[3,4-c]pyrido[2,1-f][1,2,4]triazine-6,8-dione (B-5), (R)-12-((S)-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-6), (R)-12-((S)-7,8,10-trifluoro-6,11-dihydrodibenzo[b,e]selenepin-11-yl)-3,4,12,12a-tetrahydro-1H[1,4]oxazino[3,4-c]pyrido[2,1-f][1,2,4]triazine-6,8-dione (B-7), (R)-12-((S)-7,10-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-8), and (R)-12-((S)-9-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-9).

Example 3

Synthesis of Methyl 2-((((R)-12-((S)-7,8-Difluoro-6,11-Dihydrodibenzo[b,e]Selenepin-11-yl)-6,8-Dioxo-3,4,6,8,12,12a-Hexahydro-1H-[1,4]Oxazino[3,4-c]Pyrido[2,1-f][1,2,4]Triazin-7-yl)Oxy)Methoxy)Acetate (C-1)

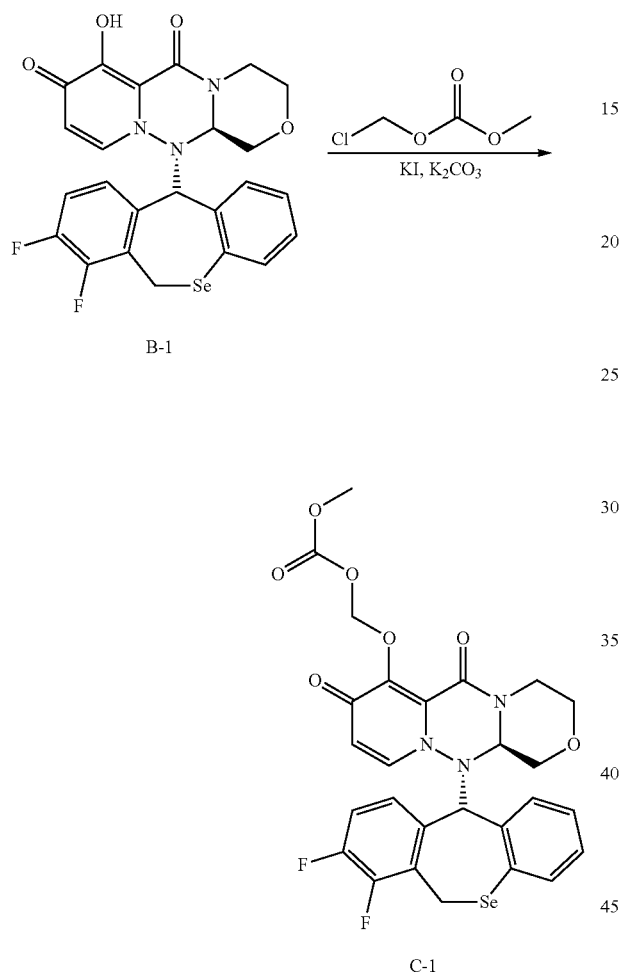

To a suspension of compound B-1 (400 mg, 0.75 mmol) in DMA (10 mL) was added chloromethyl methyl carbonate (187 mg, 1.5 mmol), $K_2CO_3$ (210 mg, 1.5 mmol), KI (125 mg, 0.75 mmol), then the reaction mixture was stirred at 50° C. overnight. The reaction was diluted with EA (20 mL), washed with water, followed by brine, purified by Prep-HPLC (0.1% TFA) to afford compound C-1 (237 mg, 50.8%) as a white solid. $^1$H-NMR (400 MHz, DMSO-d6): δ7.36-7.34 (d, J=7.6 Hz, 1H), 7.27 (s, 1H), 7.22-7.20 (d, J=8 Hz, 1H), 7.13-6.84 (m, 5H), 6.18-6.16 (d, J=7.6 Hz, 1H), 5.88 (s, 2H), 5.40 (s, 1H), 5.18-5.15 (dd, J=2.8 Hz and 12.8 Hz, 1H), 4.65-4.60 (m, 2H), 4.08-3.99 (m, 2H), 3.86 (s, 3H), 3.81-3.77 (m, 1H), 3.58-3.42 (m, 2H), 3.01-2.93 (m, 1H). LCMS [mobile phase: from 70% water (0.1% TFA) and 30% acetonitrile to 30% water (0.1% TFA) and 70% acetonitrile in 6 min, finally under these conditions for 0.5 min.] purity is >97%, Rt=3.424 min; MS Calcd.: 619; MS Found: 620 ([M+1]$^+$).

Synthesis of compounds C-2 to C-9

Compounds C-2 to C-9 are obtained in a similar manner as compound C-1.

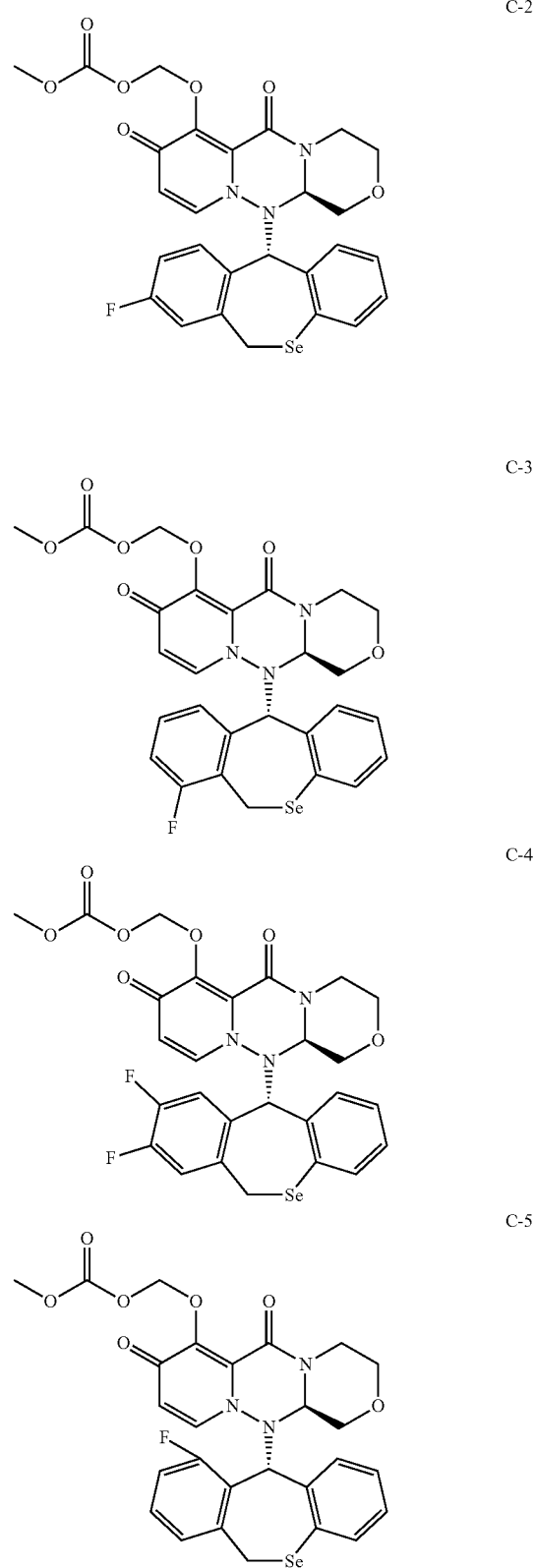

-continued

C-6
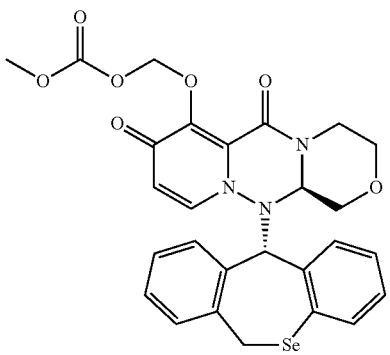

C-7
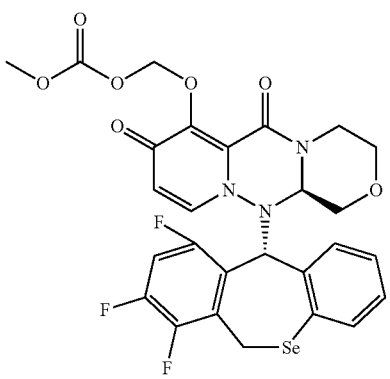

C-8
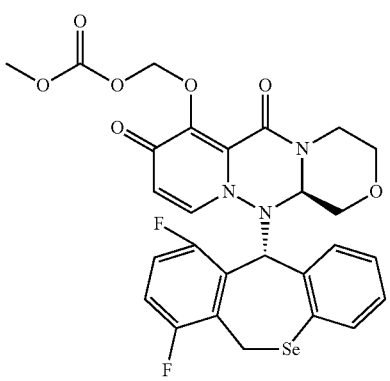

C-9
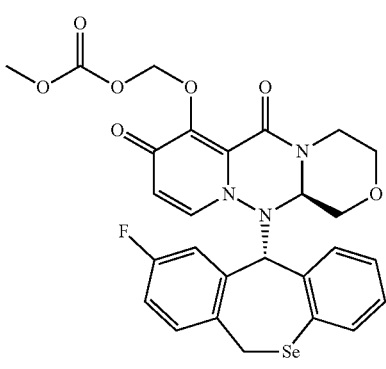

In some embodiments, provided herein is a compound selected from the group consisting of:

(((R)-12-((S)-8-fluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-2), (((R)-12-((S)-7-fluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-3), (((R)-12-((S)-8,9-difluoro-6,11-dihydrodibenzo[b, e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-4), (((R)-12-((S)-10-fluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-5), (((R)-12-((S)-6,11-dihydrodibenzo[b,e]selenepin-11-yl)-6,8-dioxo-3,4,6,8,12,12a-hexahydro-1H[1,4]oxazino[3,4-c]pyrido[2,1-f][1,2,4]triazin-7-yl)oxy)methyl methyl carbonate (C-6), (((R)-6,8-dioxo-12-((S)-7,8,10-trifluoro-6,11-dihydrodibenzo[b,e]selenepin-11-yl)-3,4,6,8,12,12a-hexahydro-1H-[1,4]oxazino[3,4-c]pyrido[2,1-f][1,2,4]triazin-7-yl)oxy)methyl methyl carbonate (C-7), (((R)-12-((S)-7,10-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-8), and (((R)-12-((S)-9-fluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-9).

Example 4

Synthesis of Compounds D-1 to D-9

Compounds D-1 to D-9 are obtained according to the following condition: To an aqueous (1.0 mL) suspension of compound B-1 (0.10 mmol) and potassium carbonate (138 mg, 0.22 mmol) are added tetrabutylammonium hydrogen sulfate (34 mg, 0.10 mmol) and dichloromethane (0.5 mL), and the mixture is stirred at room temperature for 10 minutes. To the reaction solution is added a dichloromethane (0.5 mL) solution of corresponding iodide (0.22 mmol), and the mixture is further stirred for 2 hours. Thereafter, to the reaction solution is added water, the dichloromethane layer is separated, and the aqueous layer is extracted with dichloromethane once. The combined extracts are washed with brine and then dried over sodium sulfate. The solvent is concentrated and the residue is purified by silica gel column chromatography.

D-1
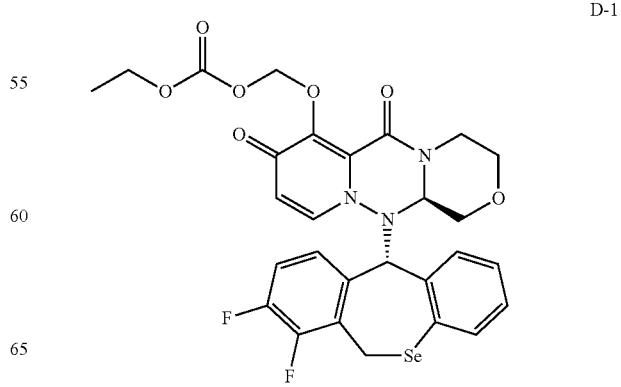

-continued
D-2
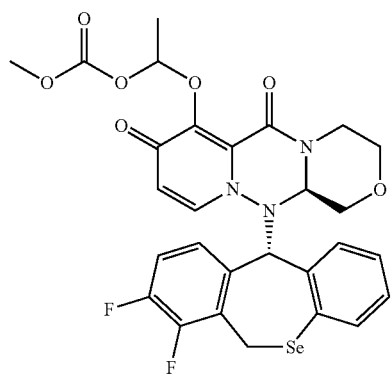
D-3
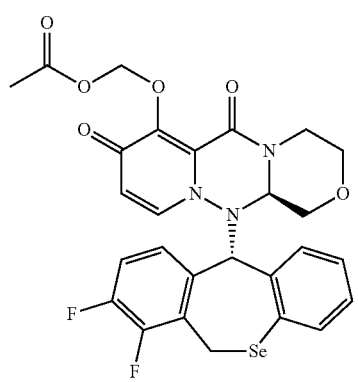
D-4
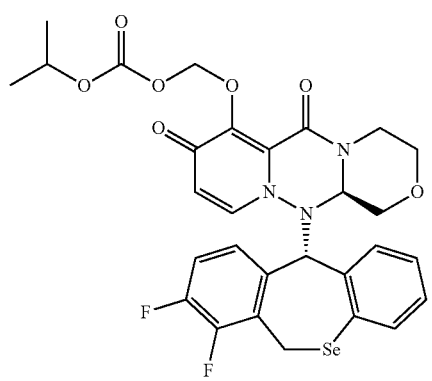
D-5
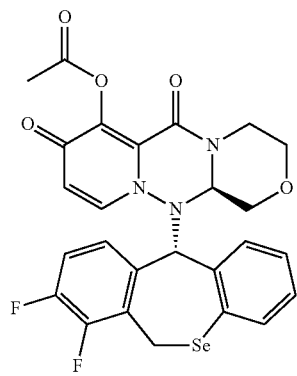
-continued
D-6
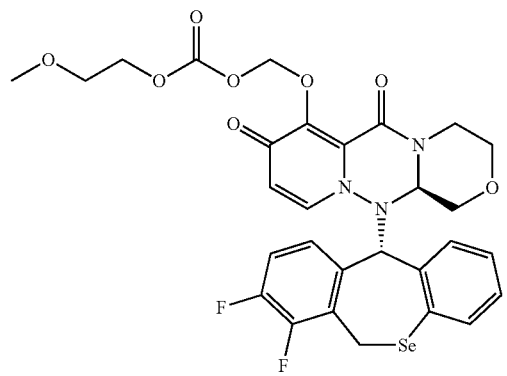
D-7
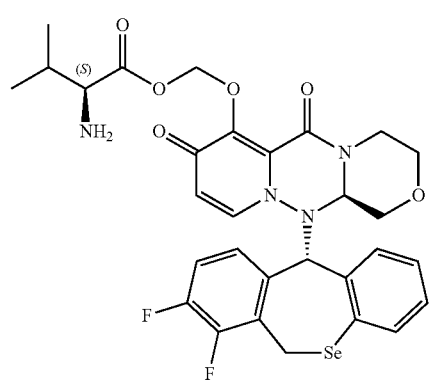
D-8
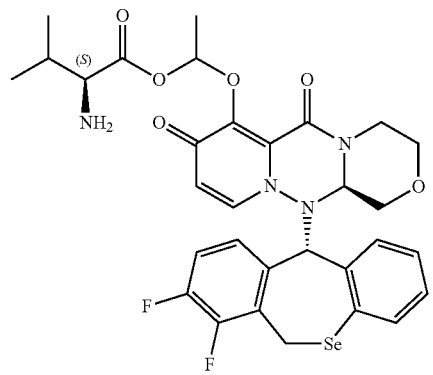
D-9
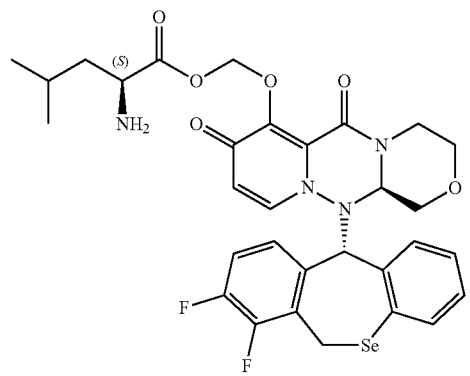

In some embodiments, provided herein is a compound selected from the group consisting of:

(((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)ethyl methyl carbonate (D-1), 1-(((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)ethyl methyl carbonate (D-2), (((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl acetate (D-3), (((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl isopropyl carbonate (D-4), (R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl acetate (D-5), (((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl (2-methoxyethyl) carbonate (D-6), (((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl L-valinate (D-7), 1-(((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)ethyl L-valinate (D-8), and (((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl L-leucinate (D-9).

Example 5

7-(Benzyloxy)-9-Bromo-12-(7,8-Difluoro-6,11-Dihydrodibenzo[b,e]Thiepin-11-yl)-3,4,12,12a-Tetrahydro-1H-[1,4]Oxazino[3,4-c]Pyrido[2,1-f][1,2,4]Triazine-6,8-Dione (15)

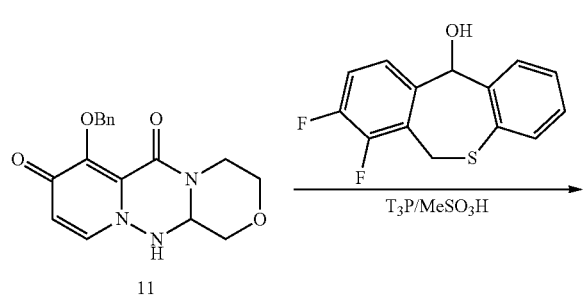

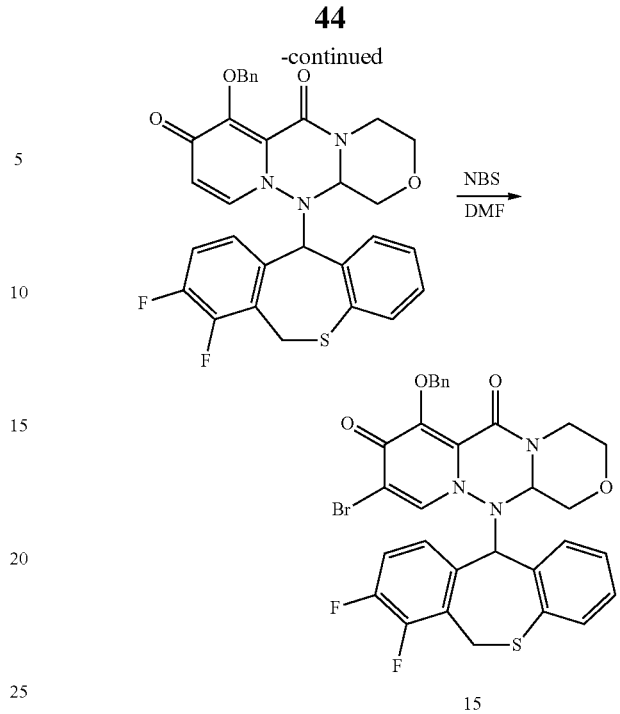

Step 1. To a suspension of compound 11 (150 mg, 0.458 mmol) in EA (3.2 mL) was added hexane (1.25 mL), stirred at r.t for 10 min, added T$_3$P (1.5 g, 2.36 mmol) and the mixture was stirred at r.t. for 30 min, added 7,8-difluoro-6,11-dihydrodibenzo[b,e]thiepin-11-ol (175 mg, 0.51 mmol) and the reaction mixture was stirred at 35° C. overnight, added MeSO$_3$H (80 mg, 0.83 mmol), 7,8-difluoro-6,11-dihydrodibenzo[b,e]thiepin-11-ol (178 mg, 0.67 mmol) in EA (0.5 mL). The mixture was stirred at 55° C. overnight and LCMS showed that most of compound 11 disappeared. The mixture was cooled down to r.t, diluted with EA (30 mL), washed with water, brine, dried over Na$_2$SO$_4$, filtered and the filtrate was evaporated. The residue was slurried in MTBE (10 mL) and PE (20 mL), filtered and dried in vacuum to afford compound 7-(benzyloxy)-12-(7,8-difluoro-6,11-dihydrodibenzo[b,e]thiepin-11-yl)-3,4,12,12a-tetrahydro-1H-[1,4]oxazino[3,4-c]pyrido[2,1-f][1,2,4]triazine-6,8-dione (205 mg, yield 78.1%) as a yellow solid, which was used directly in next step without further purification. MS Calcd: 573; MS Found: 574 (M+H$^+$).

Step 2. To a mixture of 7-(benzyloxy)-12-(7,8-difluoro-6,11-dihydrocibenzo[b,e]thiepin-11-yl)-3,4,12,12a-tetrahydro-1H-[1,4]oxazino[3,4-c]pyrido[2,1-f][1,2,4]triazine-6,8-dione (50 mg, 0.087 mmol) in CCl$_4$ (10 mL) and DMF (0.2 mL) was added NBS (31 mg). Then the mixture was stirred at r.t. overnight, washed with water and dried over Na$_2$SO$_4$. The organic phase was removed solvent and the residue was purified by Prep-HPLC to afford compound 15 (20 mg, yield 35.3%) as a light yellow solid. Combined with another batch, total 65 mg of compound 15 as obtained. $^1$H-NMR (400 MHz, CDCl$_3$): δ7.62-7.60 (m, 4H), 7.52 (s, 1H), 7.39-7.36 (m, 9H), 7.32-7.04 (m, 5H), 6.99-6.96 (m, 1H), 6.82-6.77 (m, 1H), 6.70-6.67 (m, 1H), 6.39-6.37 (d, J=7.6 Hz, 1H), 6.13-6.09 (m, 1H), 5.69-5.60 (m, 2H), 4.46-5.40 (m, 2H), 5.23-5.18 (m, 3H), 5.02 (s, 1H), 4.70-4.62 (m, 2H), 4.50-4.35 (m, 2H), 4.09-3.71 (m, 6H), 3.43-3.23 (m, 4H), 2.95-2.72 (m, 2H). LCMS [mobile phase: from 60% water (0.1% TFA) and 40% acetonitrile to 50% water (0.1% TFA) and 50% acetonitrile in 6 min, finally

Example 6

12-(7,8-Difluoro-6,11-Dihydrodibenzo[b,e]Thiepin-11-yl)-9-(Dimethylphosphoryl)-7-Hydroxy-3,4,12,12a-Tetrahydro-1H-[1,4]Oxazino[3,4-c]Pyrido[2,1-f][1,2,4]Triazine-6,8-Dione (E-1a and E-1b)

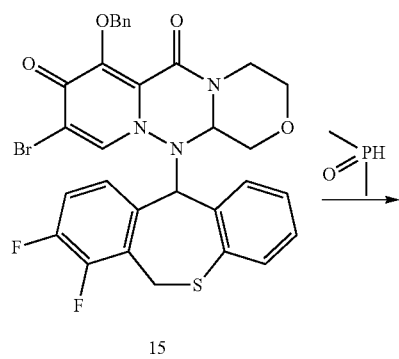

15

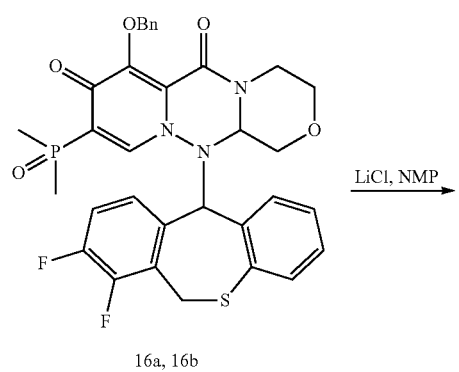

16a, 16b

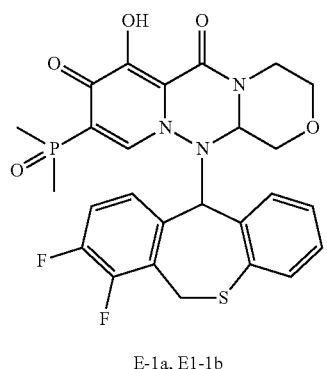

E-1a, E1-1b

Step 1: 7-(benzyloxy)-12-(7,8-difluoro-6,11-dihydrodibenzo[b,e]thiepin-11-yl)-9-(dimethylphosphoryl)-3,4,12,12a-tetrahydro-1H-[1,4]oxazino[3,4-c]pyrido[2,1-f][1,2,4]triazine-6,8-dione (16a and 16 b)

To a tube was added a solution of compound 15 (46 mg, 0.071 mmol) in 1,4-dioxane (8 mL), $Cs_2CO_3$ (205 mg, 0.63 mmol), dimethyl phosphine oxide (112 mg, 1.42 mmol), KI (60 mg, 0.36 mmol), Pd(OAc)$_2$ (24 mg, 0.107 mmol) and Xantphos (88 mg, 0.152 mmol), and the mixture was bubbled with $N_2$ for 3 min. The tube was sealed and the mixture was under microwave reacted at 95° C. for 3 h. The reaction was concentrated and added water (10 mL), extracted with EA (10 mL*3), purified by Prep-TLC (PE: EA=1:2) to obtain compound 16a (5 mg, yield 10.9%) and compound 16b (10 mg, yield 21.8%) as a yellow solid. MS Calcd: 649; MS Found: 650 ([M+H]$^+$). In this Example, when the mixture of stereoisomers are separated by HPLC, the first-eluting mixture was labeled "16a," and the second-eluting mixture was labeled "16b." 16a and 16b each are a mixture of two diastereomers.

Step 2: Synthesis of 12-(7,8-difluoro-6,11-dihydrodibenzo[b,e]thiepin-11-yl)-9-(dimethylphosphoryl)-7-hydroxy-3,4,12,12a-tetrahydro-1H-[1,4]oxazino[3,4-c]pyrido[2,1-f][1,2,4]triazine-6,8-dione (E-1a and E-1b)

To a solution of 16a (5 mg, 0.0077 mmol) in NMP (1.5 mL) was added LiCl (7.2 mg, 0.17 mmol) and the reaction was stirred at 80° C. overnight and directly purified by Prep-HPLC (0.1% TFA) to afford compound E-1a (2.7 mg, yield 52.1%) as a white solid. $^1$H-NMR (400 MHz, MeOH-d$_4$): δ 7.41-7.39 (d, J=7.2 Hz, 1H), 7.28-7.12 (m, 4H), 7.00 6.94 (m, 1H), 6.79-6.76 (m, 1H), 5.45 (s, 1H), 5.44-5.26 (dd, J=2 Hz, 1H), 4.49-4.34 (m, 3H), 4.07-4.03 (d, J=14.8 Hz, 1H), 3.96-3.92 (dd, J=2.8 Hz, 1H), 3.68-3.54 (m, 2H), 3.41-3.38 (m, 1H), 2.82-2.75 (m, 1H), 1.56-1.52 (d, J=14.4 Hz, 3H), 1.40-1.36 (d, J=14 Hz, 3H). LCMS [mobile phase: from 95% water (0.1% TFA) and 5% acetonitrile to 5% water (0.1% TFA) and 95% acetonitrile in 6 min, finally under these conditions for 0.5 min.] purity is >97%, Rt=3.567 min; MS Calcd.: 559; MS Found: 560 ([M+1]$^+$).

To a solution of compound 16b (10 mg, 0.015 mmol) in NMP (1.5 mL) was added LiCl (7.2 mg, 0.17 mmol) and the reaction was stirred at 80° C. overnight and directly purified by Prep-HPLC (0.1% TFA) to afford compound E-1b (4.4 mg, yield 43.6%) as a white solid. $^1$-NMR (400 MHz, MeOH-d$_4$): δ 7.73-7.70 (d, J=10.4 Hz, 1H), 7.33-7.19 (m, 4H), 6.93-6.86 (m, 2H), 5.67 (s, 1H), 5.51-5.47 (dd, J=2.4 Hz, 1H), 4.72-4.63 (m, 3H), 4.16-4.13 (d, J=14 Hz, 1H), 4.11-4.04 (m, 1H), 3.81-3.70 (m, 2H), 3.54-3.47 (m, 1H), 3.18-3.11 (m, 1H), 1.66-1.63 (d, J=14.4 Hz, 3H), 1.46-1.42 (d, J=14 Hz, 3H). MS Calcd: 559; MS Found: 560 ([M+H]$^+$). LCMS [mobile phase: from 80% water (0.1% TFA) and 20% acetonitrile to 30% water (0.1% TFA) and 70% acetonitrile in 6 min, finally under these conditions for 0.5 min.] purity is >98%, Rt=3.271 min; MS Calcd.: 559; MS Found: 560 ([M+1]$^+$).

Similar to 16a and 16b, E-1a and E-1b each are a mixture of two diastereomers.

Example 7

Synthesis of (R)-12-((S)-7,8-Difluoro-6,11-Dihydrodibenzo[b,e]Thiepin-11-yl)-9-(Dimethylphosphoryl)-7-Hydroxy-3,4,12,12a-Tetrahydro-1H-[1,4]Oxazino[3,4-c]Pyrido[2,1-f][1,2,4]Triazine-6,8-Dione (E-1c)

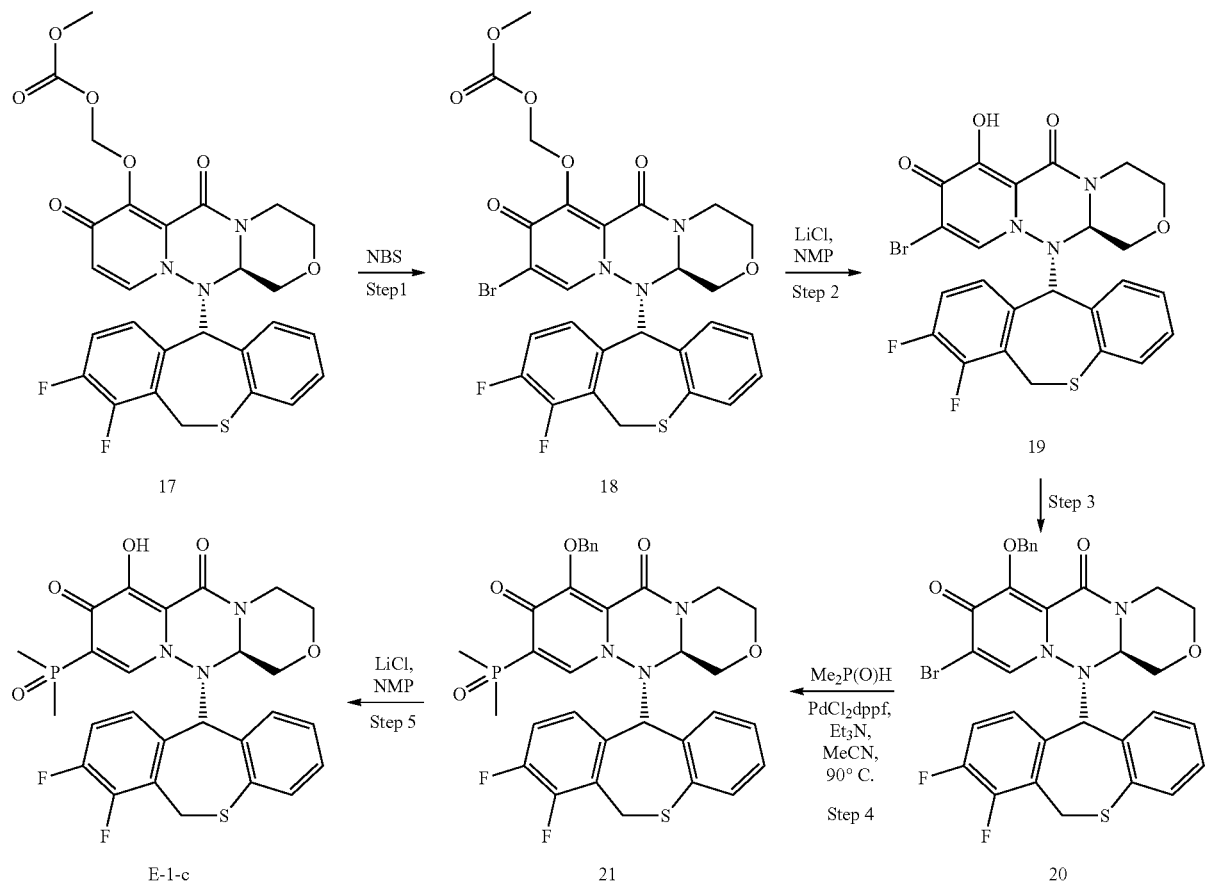

Step 1. Synthesis of (((R)-9-bromo-12-((S)-7,8-difluoro-6,11-dihydrodibenzo[b,e]thiepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (18)

To a solution of compound 17 (6 g, 10.5 mmol, commercially available) in DMF (30 mL) was added NBS (2.8 g, 15.7 mmol), then the reaction mixture was stirred at room temperature overnight. To the reaction mixture was added water (120 mL), and the reaction mixture was filtered and the obtained cake was washed with water, dried in vacuum to afford compound 18 (7.1 g, yield 100%) as a light yellow solid, which was directly used in the next step without further purification. MS Calcd: 649; MS Found: 650 ([M+H]$^+$).

Step 2. Synthesis of (R)-9-bromo-12-((S)-7,8-difluoro-6,11-dihydrodibenzo[b,e] thiepin-11-yl)-7-hydroxy-3,4,12,12a-tetrahydro-1H-[1,4]oxazino[3,4-c]pyrido[2,1-f][1,2,4]triazine-6,8-dione (19)

To a suspension of compound 18 (6.0 g, 9.2 mmol) in NMP (36 mL) was added LiCl (3.8 g, 92 mmol), then the reaction mixture was stirred at 80° C. overnight. The reaction mixture was diluted with EA (50 mL), washed with water, brine, dried over Na$_2$SO$_4$, and filtered. The filtrate was evaporated to afford crude compound 19 (5.2 g) as a pale solid, which was directly used in next step without further purification. MS Calcd: 560; MS Found: 561 ([M+H]$^+$).

Step 3. Synthesis of (R)-7-(benzyloxy)-9-bromo-12-((S)-7,8-difluoro-6,11-dihydrodibenzo[b,e]thiepin-11-yl)-3,4,12,12a-tetrahydro-1H-[1,4]oxazino[3,4-c]pyrido[2,1-f][1,2,4]triazine-6,8-dione (20)

To a solution of compound 19 (5.2 g, 9.2 mmol) in DMA (50 mL) was added K$_2$CO$_3$ (2.54 g, 18.4 mmol), KI (1.53 g, 9.2 mmol), BnBr (3.15 g, 18.4 mmol), then the reaction mixture was stirred at 50° C. overnight. The reaction mixture was diluted with EA (50 mL), washed with water, brine, purified by Prep-HPLC to afford compound 20 (4.9 g, 81.8%) as a light yellow solid. MS Calcd: 651; MS Found: 652 ([M+H]$^+$).

Step 4. Synthesis of (R)-7-(benzyloxy)-12-((S)-7,8-difluoro-6,11-dihydrodibenzo[b, e]thiepin-11-yl)-9-(dimethylphosphoryl)-3,4,12,12a-tetrahydro-1H-[1,4]oxazino[3,4-c]pyrido[2,1-f][1,2,4]triazine-6,8-dione (21)

To a solution of compound 20 (2.0 g, 3.07 mmol) in MeCN (90 mL) was added dimethylphosphine oxide (2.78 g, 35.6 mmol), TEA (2.2 g, 21.8 mmol), Pd(dppf)Cl$_2$ (500 mg), and the reaction was filled with N$_2$ for 3 times. Under N$_2$, the reaction mixture was stirred at 90° C. for 20 h. Cooled to rt, the reaction mixture was evaporated to dryness and diluted with water, extracted with EA (50 mL *3), dried over Na$_2$SO$_4$ and evaporated. The obtained reaction mixture was purified by flash column chromatography on silica gel (DCM:MeOH=10:1) to afford compound 21 (1.8 g, yield 90%) as a yellow solid. MS Calcd: 649; MS Found: 650 ([M+H]$^+$).

Step 5. Synthesis of (R)-12-((S)-7,8-difluoro-6,11-dihydrodibenzo[b,e]thiepin-11-yl)-9-(dimethylphosphoryl)-7-hydroxy-3,4,12,12a-tetrahydro-1H-[1,4]oxazino[3,4-c]pyrido[2,1-f][1,2,4]triazine-6,8-dione (E-1c)

To a suspension of compound 21 (2 g, 3 mmol) in NMP (7 mL) was added LiCl (1.3 g, 30 mmol), then the reaction mixture was stirred at 80° C. overnight. The reaction was purified by Prep-HPLC (0.1% TFA) to afford compound E-1c (1.1 g, 63.8%) as an off white solid. $^1$H-NMR (400 MHz, DMSO-d6): δ 7.47-7.39 (m, 3H), 7.18-7.14 (m, 1H), 7.10-7.08 (m, 1H), 6.99-6.97 (m, 1H), 6.87-6.83 (m, 1H), 5.80 (s, 1H), 5.43-5.39 (dd, J=2.4 Hz and 14 Hz, 1H), 4.59-4.55 (dd, J=2.8 Hz and 10 Hz, 1H), 4.46-4.42 (m, 1H), 4.11-4.01 (m, 2H)), 3.77-3.67 (m, 2H), 3.47-3.41 (m, 1H), 3.10-3.03 (m, 1H), 1.46-1.43 (d, J=14.4 Hz, 3H), 1.23-1.19 (d, J=14.4 Hz, 3H). LCMS [mobile phase: from 80% water (0.1% TFA) and 20% acetonitrile to 30% water (0.1% TFA) and 70% acetonitrile in 6 min, finally under these conditions for 0.5 min.] purity is >98%, Rt=3.184 min; MS Calcd.: 559; MS Found: 560 ([M+1]$^+$).

Synthesis of compounds E-2 to E-10

Compounds E-2 to E-10 are obtained according to the following condition: To an aqueous (1.0 mL) suspension of compound E-1c (0.10 mmol) and potassium carbonate (138 mg, 0.22 mmol) are added tetrabutylammonium hydrogen sulfate (34 mg, 0.10 mmol) and dichloromethane (0.5 mL), and the mixture is stirred at room temperature for 10 minutes. To the reaction solution is added a dichloromethane (0.5 mL) solution of corresponding iodide (0.22 mmol), and the mixture is further stirred for 2 hours. Thereafter, to the reaction solution is added water, the dichloromethane layer is separated, and the aqueous layer is extracted with dichloromethane once. The combined extracts are washed with brine and then dried over sodium sulfate. The solvent is concentrated and the residue is purified by silica gel column chromatography.

E-2

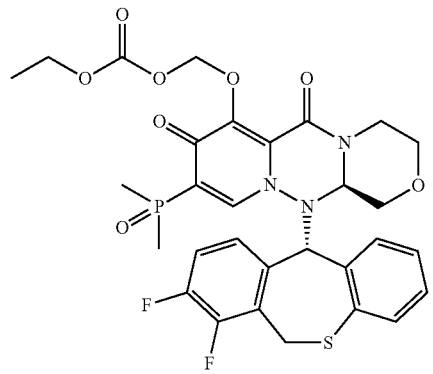

E-3

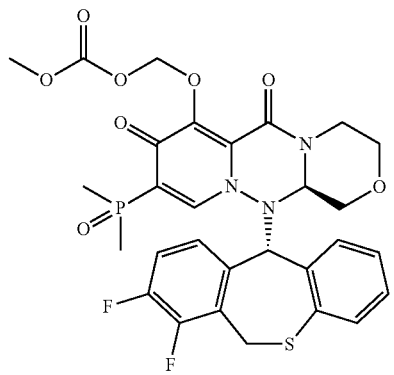

E-4

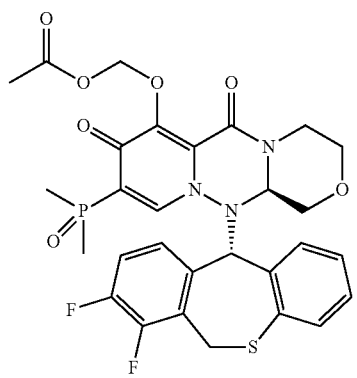

E-5

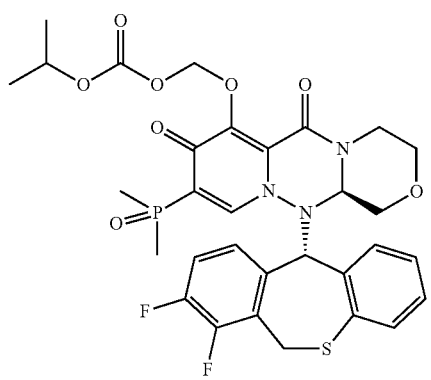

E-6

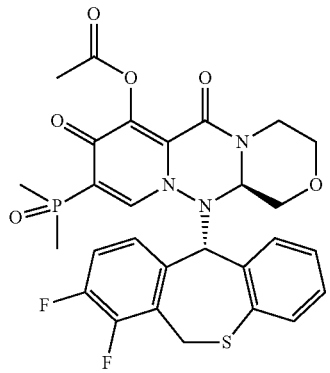

-continued

E-7
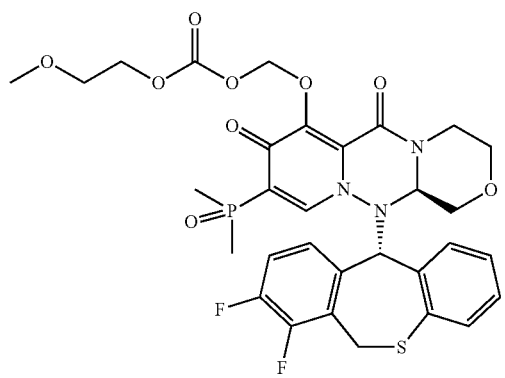

E-8
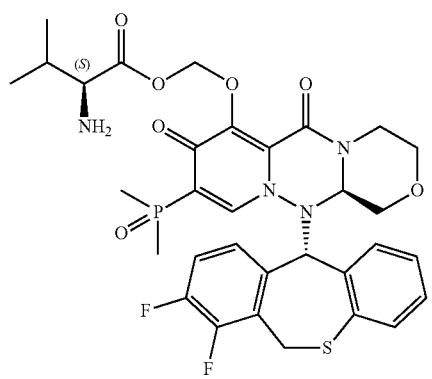

E-9
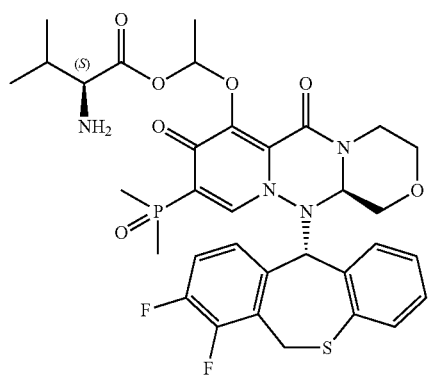

E-10
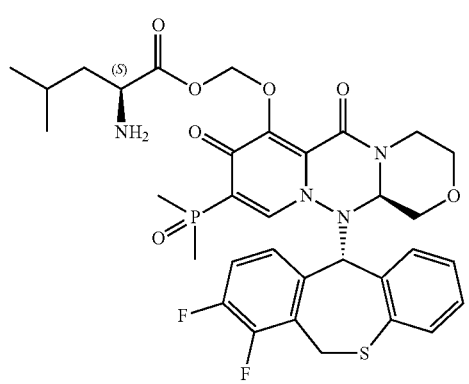

In some embodiments, provided herein is a compound selected from the group consisting of:

(((R)-12-((S)-7,8-difluoro-6,11-dihydrodibenzo[b,e]thiepin-11-yl)-9-(dimethylphosphoryl)-6,8-dioxo-3,4,6,8,12,12a-hexahydro-1H-[1,4]oxazino[3,4-c]pyrido[2,1-f][1,2,4]triazin-7-yl)oxy)methyl ethyl carbonate (E-2), (((R)-12-((S)-7,8-difluoro-6,11-dihydrodibenzo[b,e]thiepin-11-yl)-9-(dimethylphosphoryl)-6,8-dioxo-3,4,6,8,12,12a-hexahydro-1H-[1,4]oxazino[3,4-c]pyrido[2,1-f][1,2,4]triazin-7-yl)oxy)methyl carbonate (E-3), (((R)-12-((S)-7,8-difluoro-6,11-dihydrodibenzo[b,e]thiepin-11-yl)-9-(dimethylphosphoryl)-6,8-dioxo-3,4,6,8,12,12a-hexahydro-1H-[1,4]oxazino[3,4-c]pyrido[2,1-f][1,2,4]triazin-7-yl)oxy)methyl acetate (E-4), (((R)-12-((S)-7,8-difluoro-6,11-dihydrodibenzo[b,e]thiepin-11-yl)-9-(dimethylphosphoryl)-6,8-dioxo-3,4,6,8,12,12a-hexahydro-1H-[1,4]oxazino[3,4-c]pyrido[2,1-f][1,2,4]triazin-7-yl)oxy)methyl isopropyl carbonate (E-5), (R)-12-((S)-7,8-difluoro-6,11-dihydrodibenzo[b,e]thiepin-11-yl)-9-(dimethylphosphoryl)-6,8-dioxo-3,4,6,8,12,12a-hexahydro-1H-[1,4]oxazino[3,4-c]pyrido[2,1-f][1,2,4]triazin-7-yl acetate (E-6), (((R)-12-((S)-7,8-difluoro-6,11-dihydrodibenzo[b,e]thiepin-11-yl)-9-(dimethylphosphoryl)-6,8-dioxo-3,4,6,8,12,12a-hexahydro-1H-[1,4]oxazino[3,4-c]pyrido[2,1-f][1,2,4]triazin-7-yl)oxy)methyl (2-methoxyethyl) carbonate (E-7), (((R)-12-((S)-7,8-difluoro-6,11-dihydrodibenzo[b,e]thiepin-11-yl)-9-(dimethylphosphoryl)-6,8-dioxo-3,4,6,8,12,12a-hexahydro-1H-[1,4]oxazino[3,4-c]pyrido[2,1-f][1,2,4]triazin-7-yl)oxy)methyl L-valinate (E-8), 1-(((R)-12-((S)-7,8-difluoro-6,11-dihydrodibenzo[b,e]thiepin-11-yl)-9-(dimethylphosphoryl)-6,8-dioxo-3,4,6,8,12,12a-hexahydro-1H-[1,4]oxazino[3,4-c]pyrido[2,1-f][1,2,4]triazin-7-yl)oxy)methyl L-valinate (E-9), and (((R)-12-((S)-7,8-difluoro-6,11-dihydrodibenzo[b,e]thiepin-11-yl)-9-(dimethylphosphoryl)-6,8-dioxo-3,4,6,8,12,12a-hexahydro-1H-[1,4]oxazino[3,4-c]pyrido[2,1-f][1,2,4]triazin-7-yl)oxy)methyl L-leucinate (E-10).

Example 8

Synthesis of (R)-9-(Diethylphosphoryl)-12-((S)-7,8-Difluoro-6,11-Dihydrodibenzo[b,e]-Thiepin-11-yl)-7-Hydroxy-3,4,12,12a-Tetrahydro-1H-[1,4]Oxazino[3,4-c]Pyrido[2,1-f][1,2,4]Triazine-6,8-Dione (F-1)

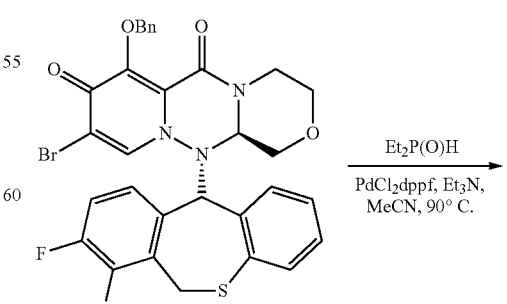

20

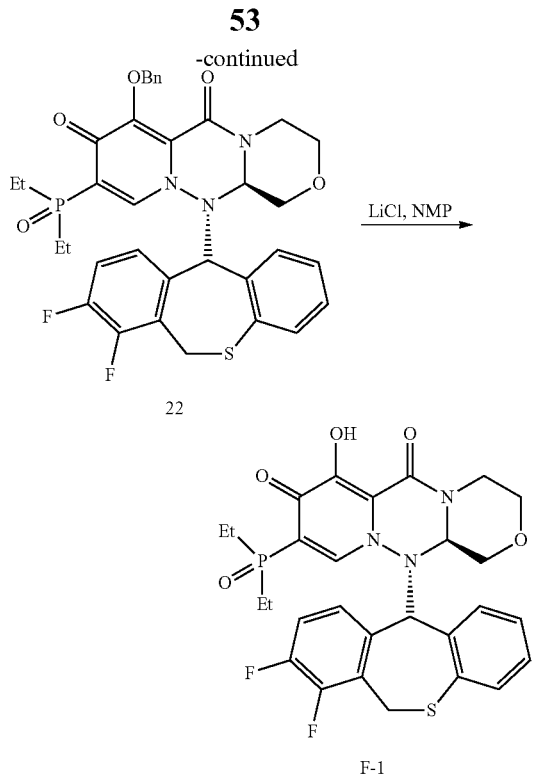

Step 1: To a solution of compound 20 (200 mg, 0.307 mmol) in MeCN (9 mL) was added diethylphosphine oxide (390 mg, 3.68 mmol), TEA (220 mg, 2.18 mmol), Pd(dppf)Cl$_2$ (60 mg), filled with N$_2$ for 3 times. Under N$_2$, the reaction was stirred at 90° C. for 20 h. Cooled to rt, the mixture was evaporated to dryness and diluted with water, extracted with EA (5 mL *3), dried over Na$_2$SO$_4$ and evaporated. The crude was purified by flash column chromatography on silica gel (DCM:MeOH=10:1) to afford compound 22 (150 mg, yield 72.1%) as a yellow solid. MS Calcd: 677; MS Found: 678 ([M+H]$^+$).

Step 2: To a suspension of compound 22 (150 mg, 0.22 mmol) in NMP (1 mL) was added LiCl (93 mg, 2.2 mmol), then stirred at 80° C. overnight. The reaction was directly purified by Prep-HPLC (0.1% TFA) to afford compound F-1(77 mg, 59.2%) as a white solid. $^1$H-NMR (400 MHz, DMSO-d6): δ 7.50-7.47 (d, J=9.6 Hz, 3H), 7.42-7.39 (m, 2H), 7.11-7.08 (m, 2H), 7.03-7.02 (m, 1H), 6.88-6.84 (m, 1H), 5.82 (s, 1H), 5.39-5.35 (m, 1H), 4.59-4.55 (dd, J=2.8 Hz and 9.6 Hz, 1H), 4.45-4.42 (m, 1H), 4.12-4.04 (m, 2H), 3.72-3.66 (m, 2H), 3.49-3.42 (m, 1H), 3.09-3.02 (m, 1H), 1.79-1.70 (m, 2H), 1.65-1.42 (m, 2H), 0.87-0.79 (m, 3H), 0.70-0.62 (m, 3H). LCMS [mobile phase: from 70% water (0.1% TFA) and 30% acetonitrile to 40% water (0.1% TFA) and 60% acetonitrile in 6 min, finally under these conditions for 0.5 min.] purity is >99%, Rt=2.864 min; MS Calcd.: 587; MS Found: 588 ([M+1]$^+$).

Biological Examples

The activity of a compound according to the present invention can be assessed by the following in vitro and in vivo methods.

Example 9

Using the test assays described herein, representative compounds of the invention are tested by in vitro assays.

Influenza virus Cap-Dependent Endonuclease (CEN) Inhibition Assay

Prepared assay buffer 2 solution (20 mM Tris, 150 mM NaCl, 2 mM MnCl$_2$, 10 mM β-Mercaptoethanol, 0.2% Trition-X100, pH7.9), 6×compound working solution, and 100 nM of Influenza Virus CEN PAn enzyme working solution (2X). Added 9 μL of enzyme working solution to each well of 384-well plate (Corning, 3676), then added 3 μL of 6×compound working solution to the indicated well of the 384-well plate, centrifuged at 200 g, RT for 60 s, then incubated the plate at 25° C. for 20 min. The results are shown below in Table 1.

The following procedures should be protected from light:
Prepared 600 nM of influenza PA ssDNA substrate_2 working solution (3X).

Added 6 μL of 3X substrate working solution to each well of the 384-well plate to start the reaction at 37° C. and incubated for 4 hr.

Collected the data by Victor Nivo microplate reader at Ex/Em=485 nm/535 nm.

Data Analysis was conducted as follows:
Z' factor=1-3*(SD$_{max}$+SD$_{min}$)/(Mean$_{max}$-Mean$_{min}$)
CV$_{Max}$=(SD$_{max}$/Mean$_{max}$)*100%
CV$_{Min}$=(SD$_{min}$/Mean$_{min}$)*100%
S/B=Singal/Background
Vehicle Control (Max): 0.1% DMSO
Positive Control (Min): 1,000 nM of Baloxavir acid
Calculation Equation for IC$_{50}$ Value:
Y=Bottom+(Top-Bottom)/(1+10^((Log IC$_{50}$-X)*Hill-Slope))
X: log value of compound; Y: Inhibition %

As listed in Table 1, representative compounds (except prodrug C-1) showed potent inhibitory effect on the cap dependent endonuclease activity.

TABLE 1

Inhibitory potency on the enzymatic activity of cap dependent endonuclease

| Index | Compound | CEN IC$_{50}$ (nM) |
|---|---|---|
| 1 | Baloxavir acid | 14 |
| 2 | A-1-P1 | 42 |
| 3 | A-1-P2 | 25 |
| 4 | E-1a | 31 |
| 5 | E-1b | 32 |
| 6 | B-1 | 15 |
| 7 | C-1 | 1548 |

In vitro Antiviral Activity

MDCK cells were seeded in 96 well plates at a density of 15,000 cells/well and cultured at 37° C. and 5% CO$_2$ overnight. Next day, serially diluted compounds and viruses were added in to cells. The resulting cultures were kept at 35° C. or 37° C. and 5% CO$_2$ for additional 5 days until virus infection in the virus control (cells infected with virus, without compound treatment) display significant cytopathic effect (CPE). Antiviral activity of the compounds was calculated based on the protection of the virus-induced CPE at each concentration normalized by the virus control.

Cytotoxicity of the compounds was assessed under the same conditions, but without virus infection, in parallel. Cell viability was measured with CCK8 following the manufacturer's manual.

Antiviral activity and cytotoxicity of the compounds are expressed as % Inhibition and % Viability, respectively, and calculated with the formulas below:

Inhibition (%)=(Raw data$_{CPD}$−Average$_{VC}$)/(Average$_{CC}$−Average$_{VC}$)*100

Viability (%)=(Raw data$_{CPD}$−Average$_{MC}$)/(Average$_{CC}$−Average$_{MC}$)*100

Raw data$_{CPD}$ indicates the values of the sample-treated wells; Average$_{VC}$, Average$_{CC}$ and Average$_{MC}$ indicate the average values of the virus control, cell control (cells without virus infection or compound treatment) and medium control (medium only) wells, respectively.

$EC_{50}$ and $CC_{50}$ values were calculated using the GraphPad Prism software with equation "log(inhibitor) vs. response—Variable slope". Data are listed in Table 2. Representative compounds, in particular, B-1 showed potent antivirus activity and little cytotoxicity.

TABLE 2

In vitro antivirus activity and cytotoxicity

|  |  | B-1 | E-1c | F-1 | Baloxavir acid | Oseltamivir acid |
|---|---|---|---|---|---|---|
| $EC_{50}$ (nM) | IFV A/PR/8/34 (H1N1) | 1.1 | 68 | >100 | 0.73 | >100,000 |
|  | IFV A/WSN/33 (H1N1) | 0.32 | 58 | 57 | 0.44 | >100,000 |
|  | A/Weiss/43 (H1N1) | 1.2 | 133 | 22 | 0.74 | 476 |
|  | Oseltamivir-resistant A/Weiss/43 (H1N1) | 1.1 | 254 | 881 | 1.0 | >100,000 |
|  | A/California/07/2009 (H1N1)pdm09 | 0.37 | 129 | 125 | 0.66 | 231 |
|  | A/Hongkong/8/68 (H3N2) | 0.68 | 207 | 310 | 1.7 | 20 |
|  | B/Florida/78/2015 | 25 | >1000 | >1000 | 16 | 8481 |
|  | B/Lee/40 | 12 | >1000 | >1000 | 6.3 | 749 |
| $CC_{50}$ (µM) |  | 13 | >100 | >100 | 12 | >100 |

Example 10

In Vivo Antiviral Activity

Balb/c mice of 6~8 week old were used in this study. The influenza virus PR/8/34 diluent was pipetted by a pipette and inoculated via intranasal route at the amount of 1,000 PFU in 50 µL/animal after animals were deeply anesthetized on the day of inoculation (day 0). B-1 dosing solutions were prepared in 5% DMSO/40% PEG400/55% water at 0.5 mg/mL. C-1 dosing solutions were prepared in 5% DMSO/40% PEG400/55% water at 0.15 mg/mL and 0.5 mg/mL. Oseltamivir Phosphate dosing solutions were prepared in PBS X1 at 1 mg/ml. The vehicle was 5% DMSO/40% PEG400/55% water solution. B-1, C-1, Oseltamivir Phosphate or vehicle was administered via PO route following the regimen of BID (8/16 h) from day 1 to day 7 at 10 mL/kg/day, with first dose given at 24 hours post virus inoculation. Animal body weight and survival were continuously monitored from day 0 to day 14. Animals that lose more than 35 percent of their body weight will be euthanized and included into the death number. The body weight and survival rate of the animals were statistically analyzed to evaluate the in vivo efficacy of B-1, C-1, Oseltamivir Phosphate and vehicle in the influenza mouse infection model. The results were summarized in FIG. 1A and FIG. 1B.

For the vehicle group, infection of influenza virus PR/8/34 produced substantial body weight loss and all the mice died on Day 8. Treatment of C-1 resulted in significant dose-dependent improvement in body weight loss. The body weight loss at 5 mg/kg of C-1 treatment was minimal. Similarly, treatment of B-1 at 5 mg/kg also showed potent antivirus efficacy with minimal body weight loss. All the mice in the groups of B-1 and C-1 treatment survived throughout the study. Treatment of oseltamivir did not result in substantial improvement in body weight loss and 60% mice died.

Example 11

The study of drug metabolism and pharmacokinetics of representative compounds was conducted.

Liver Microsomal Stability

Liver microsomal assay was used to evaluate the metabolic stability of A-1-P2. A-1-P2 at the concentration of 104 was incubated with 0.5 mg/mL liver microsome in the presence of NADPH and UDPGA as the co-factors for 0, 15, 30, 45 and 60 minutes. The incubation was carried out at 37° C. with 5% $CO_2$ and saturating humidity. Disappearance of the compound was monitored by LC/MS/MS and $t_{1/2}$ and intrinsic clearance were calculated from the disappearance of the compound. In certain embodiments, the determined till and intrinsic clearance of A-1-P2 in different species is described herein in Table 3.

TABLE 3

Liver microsome stability of A-1-P2

| Species | Half-life $t_{1/2}$ (min) | Intrinsic clearance Cl'$_{int}$, (µL/min/mg protein) |
|---|---|---|
| Human | 3655 | 2.2 |
| Cynomolgus | 85 | 16 |
| Dog | 375 | 4.5 |
| Rat | 173 | 8.3 |
| Mice | 286 | 5.2 |

Pharmacokinetics in Rats

B-1 was administered to non-fasted male SD rats (6-8 weeks old, 200-300 grams, 3 animals each group) via intravenous (IV) bolus at 0.25 mg/kg and by oral gavage (PO) at 3 mg/kg. C-1 was administered to 3 non-fasted male SD rats via oral gavage at 3 mg/kg. Blood samples (~0.2 mL each time point) were collected via the jugular vein into tubes containing potassium ethylenediaminetetraacetic acid ($K_2$EDTA) as the anticoagulant at 0.033, 0.083, 0.25, 0.5, 1, 2, 4, 8 and 24 hours post dose for IV administration and 0.083, 0.25, 0.5, 1, 2, 4, 8 and 24 hours post dose for PO administration. The blood samples were then centrifuged for 5 minutes in a centrifuge refrigerated at 4° C. The resultant plasma samples were analyzed using LC/MS/MS to determine concentrations of B-1. Non-compartmental model with WinNonlin (PhoenixTM, version 8.0) software was used to calculate pharmacokinetic (PK) parameters. The PK results are listed in Table 4. The oral bioavailability of B-1 following oral gavage administration of B-1 in rats is 14%; and the oral bioavailability of B-1 following oral gavage administration of the prodrug C-1 is 30%. In contrast, the oral bioavailability of baloxavir in rats is 0.69% following oral administration of baloxavir, and the oral bioavailability of baloxavir in rats is 9.8-14.7% following administration of its prodrug baloxavir marboxil (Baloxavir marboxil NDA document).

TABLE 4

PK parameters in SD rats

|  | Unit | B-1 IV 0.25 mg/kg n = 3 | B-1 PO 3 mg/kg n = 3 | C-1 PO 3 mg/kg n = 3 |
|---|---|---|---|---|
| $t_{1/2}$ | h | 4.0 | 3.1 | 3.5 |
| $T_{max}$ | h |  | 2.6 | 1.7 |
| $C_{max}$ | ng/mL |  | 21 | 37 |
| $AUC_{last}$ | h*ng/mg | 84 | 123 | 280 |
| $AUC_{Inf}$ | h*ng/mL | 92 | 149 | 289 |
| F | % |  | 14 | 30 |

Pharmacokinetics in Mice

B-1 was administered to male CD-1 mice (4-6 weeks old, 20-30 grams, 3 animals each group) via intravenous (IV) bolus at 1 mg/kg and by oral gavage (PO) at 10 mg/kg. C-1 was administered to 3 male CD-1 mice via oral gavage at 10 mg/kg. All animals had free access to food and water prior to dosing. Blood samples (~0.03 mL each time point) were collected via the jugular vein into tubes containing sodium heparin as the anticoagulant at 0.033, 0.083, 0.25, 0.5, 1, 2, 4, 8 and 24 hours post dose for IV administration and 0.083, 0.25, 0.5, 1, 2, 4, 8 and 24 hours post dose for PO administration. The blood samples were then centrifuged for 5 minutes in a centrifuge refrigerated at 4° C. The resultant plasma samples were analyzed using LC/MS/MS to determine concentrations of B-1. Non-compartmental model with WinNonlin (Phoenix™, version 8.0) software was used to calculate pharmacokinetic (PK) parameters. The PK results are listed in Table 5. The oral bioavailability of B-1 following oral gavage administration of B-1 in mice is 35%; and the oral bioavailability of B-1 following oral gavage administration of the prodrug C-1 is 55%.

TABLE 5

PK parameters in male CD-1 mice

|  | Unit | B-1 IV 1 mg/kg n = 3 | B-1 PO 10 mg/kg n = 3 | C-1 PO 10 mg/kg n = 3 |
|---|---|---|---|---|
| $T_{1/2}$ | h | 4.1 | 3.4 | 3.2 |
| $T_{max}$ | h |  | 5.3 | 1.7 |
| $C_{max}$ | ng/mL |  | 165 | 330 |
| $AUC_{last}$ | h*ng/mg | 601 | 2129 | 2834 |
| $AUC_{Inf}$ | h*ng/mL | 608 | 2147 | 2851 |
| F | % |  | 35 | 55 |

Pharmacokinetics in Monkeys

B-1 was administered to male cynomolgus monkeys (2-5 years old, 2-5 kg, 3 animals each group) via intravenous (IV) bolus at 0.25 mg/kg and by oral gavage (PO) at 1 mg/kg; Animals in the IV group had free access to food and water (non-fasted) and animals in the PO group were fasted overnight prior to dosing (fasted). C-1 was administered to male cynomolgus monkeys (fasted or non-fasted, 3 each group) via oral gavage at 1 mg/kg. Blood samples (~0.5 mL each time point) were collected via the jugular vein into tubes containing potassium ethylenediaminetetraacetic acid ($K_2EDTA$) as the anticoagulant at 0.033, 0.083, 0.25, 0.5, 1, 2, 4, 8 and 24 hours post dose for IV administration and 0.083, 0.25, 0.5, 1, 2, 4, 8 and 24 hours post dose for PO administration. The blood samples were then centrifuged for 10 minutes in a centrifuge refrigerated at 2-8° C. The resultant plasma samples were analyzed using LC/MS/MS to determine concentrations of B-1. Non-compartmental model with WinNonlin (Phoenix™, version 6.1) software was used to calculate pharmacokinetic (PK) parameters. The PK results are listed in Table 6. The oral bioavailability of B-1 following oral gavage administration of B-1 in monkeys is 27%. The oral bioavailability of B-1 following oral gavage administration of the prodrug C-1 is 57% and 53% at fasted and non-fasted conditions, respectively; and feeding condition did not impact oral absorption of C-1. On the other hand, the oral bioavailability of baloxavir following administration of its prodrug baloxavir marboxil was largely affected by feeding conditions. The oral bioavailability of baloxavir was 10.5-11.5% and 50.6%, respectively, following oral administration of baloxavir marboxil to non-fasted and fasted monkeys (Baloxavir marboxil NDA document).

TABLE 6

PK parameters in cynomolgus monkeys

|  | Unit | B-1 IV 0.25 mg/kg n = 3 | B-1 PO 1 mg/kg n = 3 | C-1 PO 1 mg/kg n = 3 Fasted | C-1 PO 1 mg/kg n = 3 Non-fasted |
|---|---|---|---|---|---|
| $t_{1/2}$ | h | 11 | 9.4 | 9.6 | 8.9 |
| $T_{max}$ | h |  | 3.3 | 2.0 | 2.0 |
| $C_{max}$ | ng/mL |  | 267 | 52 | 54 |
| $AUC_{last}$ | h*ng/mg | 204 | 231 | 414 | 400 |
| $AUC_{Inf}$ | h*ng/mL | 257 | 274 | 503 | 469 |
| F | % |  | 27 | 57 | 53 |

Figure 1B:
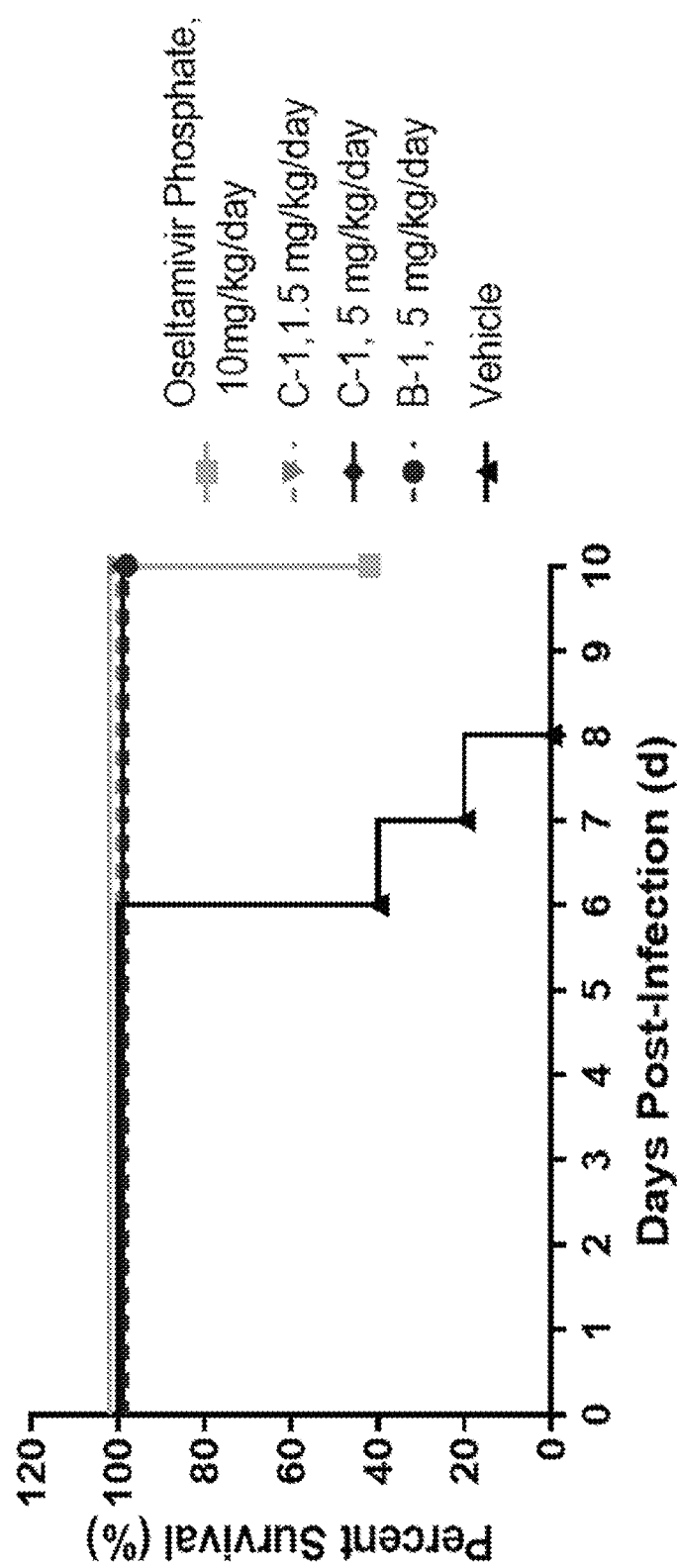

Incorporation of a selenium atom resulted in favorable pharmacokinetic and biological properties. Oral bioavailability of B-1 was 14% and 30% respectively, following oral administration of B-1 and C-1 to rats. Oral bioavailability of B-1 and C-1 was 35% and 55% in CD-1 mice, respectively. Oral bioavailability of B-1 in monkeys was 27% following oral administration of B-1. Oral bioavailability of B-1 following oral gavage administration of the prodrug C-1 to fasted and non-fasted monkeys was 57% and 53% respectively; and feeding condition did not impact oral absorption of C-1. Furthermore, both B-1 and C-1 showed potent antivirus activity in influenza virus PR/8/34 mouse model as illustrated in FIG. 1A and FIG. 1B.

Example 12

A toxicity study of C-1 was conducted in Sprague Dawley (SD) rats. C-1 at 20, 100 and 500 mg/kg or vehicle (0.5% w/v CMC-Na and 0.1% v/v Tween-80 in DI water) was administered via oral gavage to Sprague Dawley rats (7-9 weeks, about 250-300 grams each for males and about 200-250 grams each for females) once daily for 7 days. 8 females and 8 males in each dose group were used. No C-1-related toxic findings (including abnormal clinical observation, alterations in body weight, change in food consumption and change in gross pathology) were observed at all the dose levels. C-1 was well tolerated and the maximum tolerated dose (MTD) was greater than 500 mg/kg/day in Sprague Dawley rats.

It is to be understood that the invention is not limited to the particular embodiments and aspects of the disclosure described above, as variations of the particular embodiments and aspects may be made and still fall within the scope of the appended claims. All documents cited to or relied upon herein are expressly incorporated by reference.

The invention claimed is:

1. A compound of Formula (I):

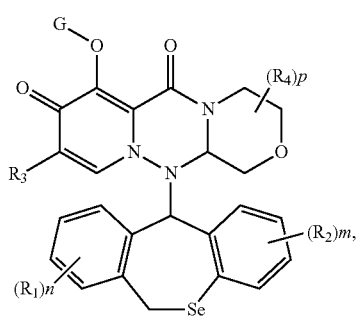

(I)

or a pharmaceutically acceptable salt, stereoisomer or solvate thereof, wherein:

each $R_1$ is independently selected from the group consisting of H and halo;
each $R_2$ is independently selected from the group consisting of H and halo;
$R_3$ is selected from the group consisting of H, halo, Me, CN, and $P(O)Me_2$;
each $R_4$ is independently selected from the group consisting of $C_1$-$C_6$ alkyl and $C_3$-$C_6$ cycloalkyl, wherein any two of $R_4$ are optionally taken, together with the atoms to which they are attached, to form a $C_3$-$C_6$ cycloalkyl;
n and m are each independently 0, 1, 2, 3, or 4;
p is 0, 1, 2, or 3; and G is H or is selected from the group consisting of C(O)R, C(O)OR, C(O)NR'R, $C(R')_2$—O—C(O)R, $C(R')_2$—O—C(O)OR, and $C(R')_2$—O—C(O)NR'R, wherein each R is selected from the group consisting of $C_1$-$C_6$ alkyl, phenyl, pyridyl, $C_3$-$C_6$ cycloalkyl, and a 4-6 membered heterocyclic ring containing one or two heteroatoms selected from the group consisting of N, O and S as ring members, wherein the $C_1$-$C_6$ alkyl, phenyl, pyridyl, $C_3$-$C_6$ cycloalkyl, and 4-6 membered heterocyclic ring of R are independently optionally substituted with one or two substituents selected from the group consisting of H, halo, CN, OH, $NH_2$, $C_1$-$C_3$ alkyl, phenyl, $C_1$-$C_4$ alkoxy, $C_1$-$C_3$ haloalkyl, and $C_1$-$C_3$ haloalkoxy; and each R' is independently selected from the group consisting of H and $C_1$-$C_3$ alkyl.

2. The compound of claim 1, or a pharmaceutically acceptable salt, stereoisomer or solvate thereof, wherein the compound is of Formula (I-1):

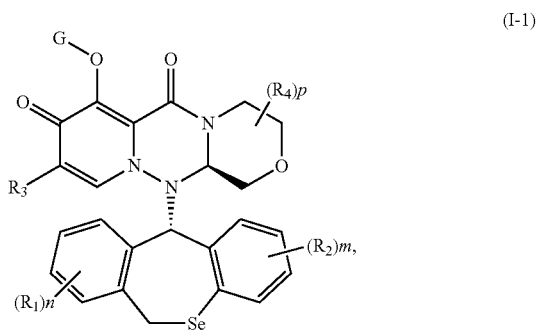

(I-1)

or a pharmaceutically acceptable salt, stereoisomer or solvate thereof.

3. The compound of claim 1, or a pharmaceutically acceptable salt, stereoisomer or solvate thereof, wherein the compound is of Formula (I-2):

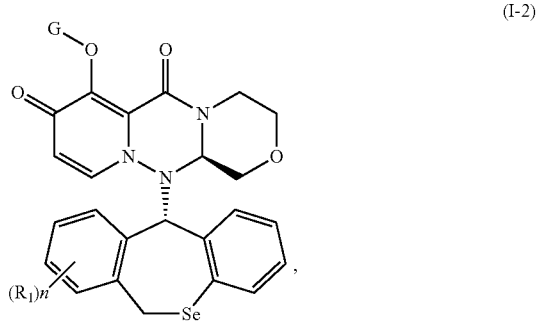

(I-2)

or a pharmaceutically acceptable salt, stereoisomer or solvate thereof.

4. The compound of claim 1, or a pharmaceutically acceptable salt, stereoisomer or solvate thereof, wherein the compound is of Formula (I-3):

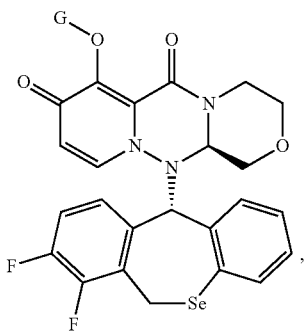

(I-3)

or a pharmaceutically acceptable salt, stereoisomer or solvate thereof.

5. The compound of claim 1, or a pharmaceutically acceptable salt, stereoisomer or solvate thereof, wherein G is H.

6. The compound of claim 1, or a pharmaceutically acceptable salt, stereoisomer or solvate thereof, wherein G is selected from the group consisting of C(O)R, C(O)OR, C(O)NR'R, C(R')$_2$—O—C(O)R, C(R')$_2$—O—C(O)OR, and C(R')$_2$—O—C(O)NR.

7. The compound of claim 6, or a pharmaceutically acceptable salt, stereoisomer or solvate thereof, wherein G is selected from the group consisting of C(O)R, C(O)OR, C(R')$_2$—O—C(O)R, and C(R')$_2$—O—C(O)OR.

8. The compound of claim 7, or a pharmaceutically acceptable salt, stereoisomer or solvate thereof, wherein G is selected from the group consisting of C(O)R, C(O)OR, CH$_2$—O—C(O)R, and CH$_2$—O—C(O)OR, where each R is independently C$_1$-C$_6$ alkyl, and the C$_1$-C$_6$ alkyl is optionally substituted with one group selected from H, halo, CN, OH, and NH$_2$.

9. The compound of claim 1, or a pharmaceutically acceptable salt, stereoisomer or solvate thereof, wherein G is selected from the group consisting of:

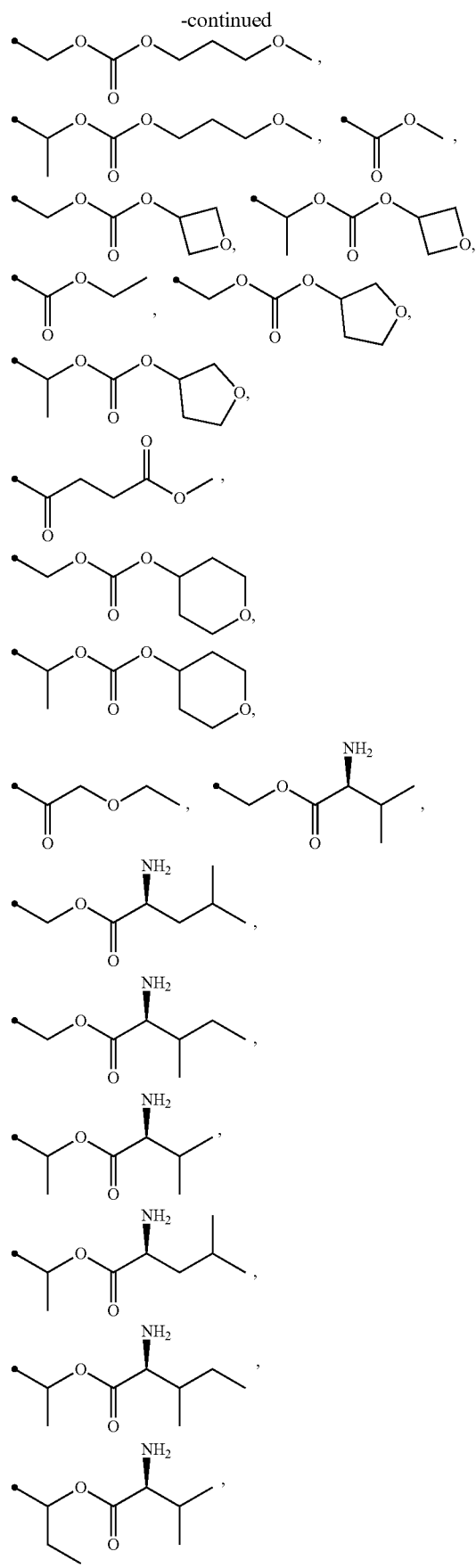

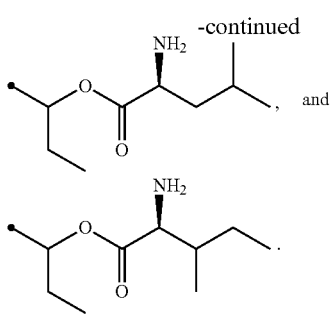

10. The compound of claim 1, or a pharmaceutically acceptable salt, stereoisomer or solvate thereof, wherein $R_3$ is selected from the group consisting of H, F, Cl, Br, Me, CN, and P(O)Me$_2$.

11. The compound of claim 10, or a pharmaceutically acceptable salt, stereoisomer or solvate thereof, wherein $R_3$ is P(O)Me$_2$.

12. The compound of claim 1, or a pharmaceutically acceptable salt, stereoisomer or solvate thereof, wherein the compound is selected from the group consisting of:
- 12-(7,8-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-1),
- 8-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-2),
- 7-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-3),
- 8,9-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-4),
- 10-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-5),
- 6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-6),
- 7,8,10-trifluoro-6,11-dihydrodibenzo[b,e]selenepin-11-yl)-3,4,12,12a-tetrahydro-1H-[1,4]oxazino[3,4-c]pyrido[2,1-f][1,2,4]triazine-6,8-dione (A-7),
- 7,10-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-8),
- 9-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (A-9),
- (R)-12-((S)-7,8-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-1),
- (R)-12-((S)-8-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-2),
- (R)-12-((S)-7-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-3),
- (R)-12-((S)-8,9-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-4),
- (R)-12-((S)-10-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-5),
- (R)-12-((S)-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-6),
- (R)-12-((S)-7,8,10-trifluoro-6,11-dihydrodibenzo[b,e]selenepin-11-yl)-3,4,12,12a-tetrahydro-1H-[1,4]oxazino[3,4-c]pyrido[2,1-f][1,2,4]triazine-6,8-dione (B-7),
- (R)-12-((S)-7,10-difluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-8)
- (R)-12-((S)-9-fluoro-6,11-dihydrodibenzo[b,e]selenepin-11-yl)-7-hydroxy-3,4,12,12a-tetrahydro-1H-[1,4]oxazino[3,4-c]pyrido[2,1-f][1,2,4]triazine-6,8-dione (B-9),
- (((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-1),
- (((R)-12-((S)-8-fluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-2),
- (((R)-12-((S)-7-fluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-3),
- (((R)-12-((S)-8,9-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-4),
- (((R)-12-((S)-10-fluoro-6,11-dihydrodibenzo[b,e]selenepin-11-yl)-6,8-dioxo-3,4,6,8,12,12a hexahydro-1H-[1,4]oxazino[3,4-c]pyrido[2,1-f][1,2,4]triazin-7-yl)oxy)methyl methyl carbonate (C-5),
- (((R)-12-((S)-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-6),
- (((R)-6,8-dioxo-12-((S)-7,8,10-trifluoro-6,11-dihydrodibenzo[b,e]selenepin-11-yl)-3,4,6,8,12,12a-hexahydro-1H-[1,4]oxazino[3,4-c]pyrido[2,1-f][1,2,4]triazin-7-yl)oxy)methyl methyl carbonate (C-7),
- (((R)-12-((S)-7,10-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-8),
- (((R)-12-((S)-9-fluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl methyl carbonate (C-9),
- (((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl ethyl carbonate (D-1),
- 1-(((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)ethyl methyl carbonate (D-2),
- (((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl acetate (D-3), (((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl isopropyl carbonate (D-4),
(R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl acetate (D-5),
(((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl (2-methoxyethyl) carbonate (D-6),
(((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl L-valinate (D-7),
1-(((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)ethyl L-valinate (D-8), and
(((R)-12-((S)-7,8-difluoro-6,11-dihydrodibenzo[b,e]selenepin-11-yl)-6,8-dioxo-3,4,6,8,12,12a-hexahydro-1H-[1,4]oxazino[3,4-c]pyrido[2,1-f][1,2,4]triazin-7-yl)oxy)methyl L-leucinate (D-9), or a pharmaceutically acceptable salt, stereoisomer or solvate thereof.

13. A pharmaceutical composition comprising a compound of claim 1, or a pharmaceutically acceptable salt, stereoisomer or solvate thereof, and one or more pharmaceutically acceptable carriers.

14. A method of treating influenza, comprising administering to a subject in need thereof a therapeutically effective amount of a compound of claim 1, or a pharmaceutically acceptable salt, stereoisomer, or solvate thereof.

15. The compound of claim 1, or a pharmaceutically acceptable salt, stereoisomer or solvate thereof, wherein $R_3$ is H.

16. The compound of claim 1, or a pharmaceutically acceptable salt, stereoisomer or solvate thereof, wherein each $R_4$ is independently $C_1$-$C_6$ alkyl or $C_3$-$C_6$ cycloalkyl.

17. The compound of claim 1, or a pharmaceutically acceptable salt, stereoisomer or solvate thereof, wherein p is 0.

18. The compound of claim 1, or a pharmaceutically acceptable salt, stereoisomer or solvate thereof, wherein R is $C_1$-$C_6$ alkyl optionally substituted with $NH_2$ or $C_1$-$C_4$ alkoxy.

* * * * *